US006630361B1

(12) United States Patent
Singh et al.

(10) Patent No.: US 6,630,361 B1
(45) Date of Patent: *Oct. 7, 2003

(54) USE OF SCATTEROMETRY FOR IN-SITU CONTROL OF GASEOUS PHASE CHEMICAL TRIM PROCESS

(75) Inventors: Bhanwar Singh, Morgan Hill, CA (US); Bharath Rangarajan, Santa Clara, CA (US); Michael K. Templeton, Atherton, CA (US); Ramkumar Subramanian, San Jose, CA (US); Cristina Cheung, San Jose, CA (US)

(73) Assignee: Advanced Micro Devices, Inc., Sunnyvale, CA (US)

(*) Notice: Subject to any disclaimer, the term of this patent is extended or adjusted under 35 U.S.C. 154(b) by 191 days.

This patent is subject to a terminal disclaimer.

(21) Appl. No.: 09/894,701

(22) Filed: Jun. 28, 2001

(51) Int. Cl.[7] ............................................... H01L 21/00
(52) U.S. Cl. ................................................ 438/7; 438/14
(58) Field of Search ............................. 438/16, 14, 7; 430/30, 317, 318, 313

(56) References Cited

U.S. PATENT DOCUMENTS

| 4,435,441 | A | * | 3/1984 | Mariani et al. | ............... | 427/10 |
| 6,342,265 | B1 | * | 1/2002 | Kelson et al. | ................. | 427/9 |
| 6,423,457 | B1 | * | 7/2002 | Bell | ............. | 430/30 |
| 6,448,097 | B1 | * | 9/2002 | Singh et al. | ................. | 438/16 |
| 6,489,624 | B1 | * | 12/2002 | Ushio et al. | ........... | 250/559.27 |
| 2002/0050160 | A1 | * | 5/2002 | Kelson et al. | ............... | 73/1.01 |
| 2002/0155389 | A1 | * | 10/2002 | Rangarajan et al. | ........ | 430/314 |
| 2003/0000922 | A1 | * | 1/2003 | Subramanian et al. | ........ | 216/60 |

OTHER PUBLICATIONS

Niu, X., et al., "Specular Spectroscopic Scatterometry in DUV Lithography," Timbre Technology, Inc., et al.

Smith, T., et al., "Process Control in the Semiconductor Industry," http://www-mtl.mit.edu/taber/Research/Process_Control/IERC99/ pp1–24.

Cote, D.R., et al., "Plasma–assisted chemical vapor deposition of dielectric thin films for ULSI semiconductor circuits," IBM Journal of Research & Development, vol. 43, No. ½ pp 1–30.

* cited by examiner

Primary Examiner—John F. Niebling
Assistant Examiner—Olivia Luk
(74) Attorney, Agent, or Firm—Amin & Turocy, LLP

(57) ABSTRACT

A system for regulating a gaseous phase chemical trim process is provided. The system includes one or more light sources, each light source directing light to one or more features and/or gratings on a wafer. Light reflected from the features and/or gratings is collected by a measuring system, which processes the collected light. The collected light is indicative of the dimensions achieved at respective portions of the wafer. The measuring system provides trimming related data to a processor that determines the acceptability of the trimming of the respective portions of the wafer. The system also includes one or more trimming devices, each such device corresponding to a portion of the wafer and providing for the trimming thereof. The processor selectively controls the trimming devices to regulate trimming of the portions of the wafer.

21 Claims, 15 Drawing Sheets

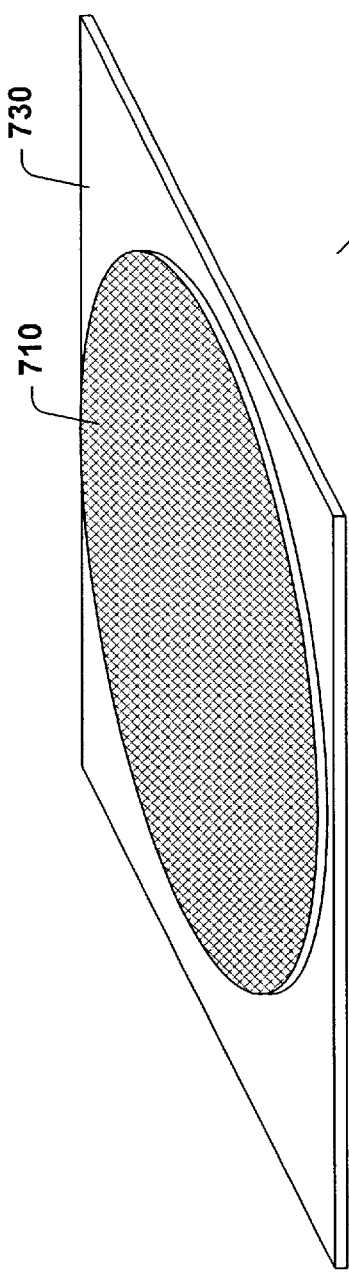
Fig. 7
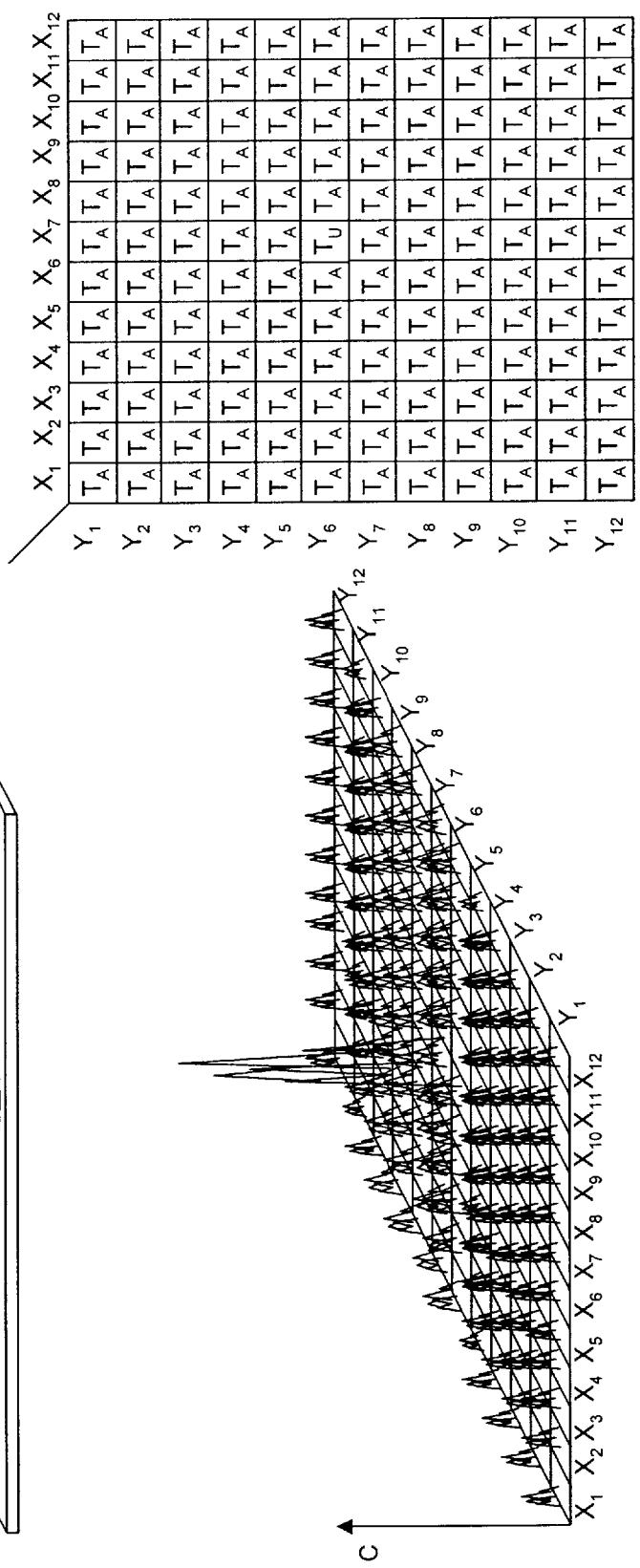
Fig. 9
Fig. 8

SURFACE NORMAL    SPECULARLY REFLECTED BEAM

USE OF SCATTEROMETRY FOR IN-SITU CONTROL OF GASEOUS PHASE CHEMICAL TRIM PROCESS

TECHNICAL FIELD

The present invention generally relates to semiconductor processing, and in particular to a system and method for in-situ monitoring and controlling of a gaseous phase chemical trim process using real-time feed forward control based on scatterometry analysis.

BACKGROUND

In the semiconductor industry, there is a continuing trend toward higher device densities. To achieve these high densities there have been and continue to be efforts toward scaling down device dimensions (e.g., at sub-micron levels) on semiconductor wafers. In order to accomplish such high device packing densities, smaller and smaller feature sizes are required. This may include the width and spacing of interconnecting lines, spacing and diameter of contact holes, and the surface geometry, such as corners and edges, of various features. The dimensions of and between such small features can be referred to as critical dimensions (CDs). Reducing CDs, and reproducing more accurate CDs facilitates achieving such higher device densities.

One method for achieving smaller features has been to perform a gaseous phase chemical trim process on a patterned photoresist. Such a gaseous phase chemical trim process can improve lithography by using a gas containing a clear ving compound to trim resist features to smaller sizes. The gas containing a cleaving compound can be employed to controllably decrease the size of developed resist structures. Conventional trim processes have either lacked feedback control systems, have employed pre-calculated gas exposure times, have employed pre-calculated gas exposure temperatures, have employed pre-calculated gas-exposure pressures, have employed a second development step and/or may have employed indirect feedback (e.g., monitoring evacuated gasses) control, which is based on indirect information to regulate gaseous phase chemical trim processes. Such pre-determined calculations and/or indirect feedback control do not provide adequate monitoring and thus do not facilitate precise control over gaseous phase chemical trim processes. Furthermore, such indirect control and/or pre-calculated parameters (e.g., exposure time, exposure temperature, exposure pressure) do not account for wafer to wafer variations, do not account for wafers with varying feature densities and do not account for lot to lot variations. Monitoring tools employed in conjunction with metrology based feedforward information are known in the art and provide improvements over conventional non feed-forward based control. But such metrology based feed-forward systems can be improved by more accurate monitoring, better CD recognition and more precise feed-forward information.

The process of manufacturing semiconductors, or integrated circuits (commonly called ICs, or chips), typically consists of more than a hundred steps, during which hundreds of copies of an integrated circuit may be formed on a single wafer. Each step can affect the CDs of the ICs. Generally, the manufacturing process involves creating several patterned layers on and into the substrate that ultimately forms the complete integrated circuit. This layering process creates electrically active regions in and on the semiconductor wafer surface. The size, shape and isolation of such electrically active regions, and thus the reliability and performance of integrated circuits employing such regions thus depend, at least in part, on the precision with which trimming can be performed.

Unfortunately, commonly used fabrication systems check devices for CDs near or at the end of fabrication, or at pre-scheduled time intervals. These types of endpoint and interval detection methods can be problematic for several reasons. For example, at later stages in the fabrication process, the presence of at least one malformed portion of a device may render the whole semiconductor device unusable, forcing it to be rejected. In addition, post-fabrication detection/quality control data do not provide a user with real-time information related to the device being fabricated. Post-fabrication data may only allow an estimation or a projection as to what adjustments are needed to correct the fabrication errors and/or flaws. Such estimations and/or projections concerning necessary adjustments may lead to continued or recurring fabrication errors. Moreover, such a lengthy adjustment process may cause subsequent fabricated wafers to be wasted in the hopes of mitigating gaseous phase chemical trim process errors.

Visual inspection methods have been important in both production and development of integrated circuits. Visually inspecting developed photoresist patterns from a dose-focus matrix is well-known in the art. While visual inspection techniques may be simple to implement, they are difficult to automate. Further, visual techniques employing scanning electron microscopes (SEM) and atomic force microscopes (AFM) can be expensive, time-consuming and/or destructive.

The requirement of small features (and close spacing between adjacent features) requires high resolution photolithographic processes. In general, lithography refers to processes for pattern transfer between various media. It is a technique used for integrated circuit fabrication in which a silicon slice, the wafer, is coated uniformly with a radiation-sensitive film, the resist, and an exposing source (such as optical light, X-rays, or an electron beam) illuminates selected areas of the surface through an intervening master template, the photomask, for a particular pattern. The lithographic coating is generally a radiation-sensitized coating suitable for receiving a projected image of the subject pattern. Once the image is projected, it is indelibly formed in the coating. The projected image may be either a negative or a positive of the subject pattern. Exposure of the coating through the photomask causes a chemical transformation in the exposed areas of the coating thereby making the image area either more or less soluble (depending on the coating) in a particular solvent developer. The more soluble areas are removed in the developing process to leave the pattern image in the coating as less soluble polymer.

Projection lithography is a powerful and essential tool for microelectronics processing. However, lithography is not without limitations. Patterning features having dimensions of about 0.25 $\mu$m or less with acceptable resolution is difficult at best, and impossible in some circumstances. Patterning small features with a high degree of critical dimension control is also very difficult. Procedures that increase resolution, improve critical dimension control and provide small features are therefore desired.

Due to the extremely fine patterns that are exposed on the photo resist, controlling a gaseous phase chemical trim process, whereby CDs on a patterned photoresist are reduced, is a significant factor in achieving desired critical dimensions. Achieving greater precision in gaseous phase chemical trim processes can result, for example, in achieving more precise CDs (e.g., desired lengths and widths between layers, between features and within features). Thus, an efficient system, and/or method, to monitor and control gaseous phase chemical trim processes is desired to facilitate manufacturing ICs exhibiting desired critical dimensions.

SUMMARY OF THE INVENTION

The following presents a simplified summary of the invention in order to provide a basic understanding of some aspects of the invention. This summary is not an extensive overview of the invention. It is not intended to identify key or critical elements of the invention or to delineate the scope of the invention. Its sole purpose is to present some concepts of the invention in a simplified form as a prelude to the more detailed description that is presented later.

The present invention provides a system that facilitates controlling a gaseous phase chemical trim processes involved in semiconductor manufacturing. An exemplary system can employ one or more light sources arranged to project light onto one or more features and/or gratings on a wafer, and one or more light sensing devices (e.g., photo detector, photodiode) for detecting light reflected and/or refracted by the one or more features and/or gratings. A grating is usually divided into a large number of sufficiently thin planar grating slabs to approximate an arbitrary profile. The light reflected from the one or more features and/or gratings is indicative of at least one parameter of a gaseous phase chemical trim processes (e.g., percent completion of trimming) that can be measured to determine whether desired critical dimensions (CDs) have been achieved and to determine whether adaptations to one or more gaseous phase chemical trim process parameters should be undertaken. One example gaseous phase chemical trim process concerns a method of treating a patterned resist involving the steps of providing the patterned resist having structural features of a first size, the patterned resist containing a polymer having a labile group; exposing the patterned photoresist to one or more chemicals in a gas containing at least one cleaving compound to form a thin deprotected resist layer at an interface between the patterned resist and the gas; and removing the thin deprotected resist layer leaving the patterned resist having structural features of a second size, wherein the second size is smaller than the first size.

One or more gaseous phase chemical trimming components can be arranged to correspond to a particular wafer portion. Alternatively, one or more gaseous phase chemical trimming components can be employed to facilitate trimming various wafer portions. The gaseous phase chemical trimming components may be, for example, apparatus that introduce a gaseous phase chemical cleaving compound (trimming compound) into a reaction chamber that holds the patterned photoresist. It is to be appreciated that a variety of trimming compounds and suitable gaseous phase chemical trimming components may be employed with the present invention. The gaseous phase chemical trimming components are selectively driven by the system to trim away patterned photoresist and/or other materials at a desired location, at a desired rate, to a desired depth and/or to a desired width. The gaseous phase trim progress is monitored by the system by comparing the critical dimensions (e.g., space between features and/or gratings, depth and/or height of the features and/or gratings) on the wafer to desired critical dimensions. Data gathered during such monitoring can be analyzed to determine whether adaptations to the chemical trim process are desired. As a result, more optimal trimming is achieved by controlling the gaseous phase chemical trimming components that are trimming the portions of the wafer, which in turn increases IC quality. Additionally, and/or alternatively, data concerning gaseous phase chemical trim process conditions that resulted in favorable and/or unfavorable CDs can be stored to facilitate reproducing favorable gaseous phase chemical trim process conditions for subsequent portions of the wafer being trimmed and/or for subsequent wafers.

One aspect of the present invention provides a system for monitoring and regulating a gaseous phase chemical trim process. The system includes a gaseous phase chemical trimming component that can trim at least one portion of a wafer and a trim component driving system for driving the gaseous phase chemical trimming component. The system includes fabricating gratings on the wafer and a system for directing light toward gratings located on the wafer. The system further includes a trim monitoring system operable to measure trimming parameters from light reflected from the gratings and a processor operatively coupled to the trim monitoring system and the trim component driving system. The processor receives trim parameter data from the measuring system and analyzes the trim parameter data by comparing the measured trim parameter data to stored trim parameter data to generate a feed-forward control data operative to control the chemical trimming component.

Another aspect of the present invention provides a method for monitoring and regulating a gaseous phase chemical trim process. The method includes logically partitioning a wafer into one or more portions. The method then establishes one or more gratings on the wafer and directs an incident light onto the gratings and collects light reflected from the grating. The reflected light is measured to determine one or more critical dimensions associated with the grating. The method includes computing adjustments for gaseous phase chemical trimming components by comparing scatterometry signatures associated with the measured critical dimensions to scatterometry signatures associated with stored critical dimensions and employing t he adjustments to adapt the chemical trim process. An example gaseous phase chemical trim process involves the steps of forming a patterned resist, the patterned resist containing a polymer having an acid labile pendent group; exposing the patterned resist to a gas containing an acid, thereby forming a thin deprotected resist layer at an interface between the patterned resist and the acid containing gas; and removing the acid containing gas and the thin deprotected resist layer thereby providing a trimmed patterned resist.

To the accomplishment of the foregoing and related ends, certain illustrative aspects of the invention are described herein in connection with the following description and the annexed drawings. These aspects are indicative, however, of but a few of the various ways in which the principles of the invention may be employed and the present invention is intended to include all such aspects and their equivalents. Other advantages and novel features of the invention may become apparent from the following detailed description of the invention when considered in conjunction with the drawings.

BRIEF DESCRIPTION OF THE DRAWINGS

FIG. 7 is a perspective illustration of a wafer upon which a photo resist that may be trimmed is located, in accordance with an aspect of the present invention.

FIG. 8 is a representative three-dimensional grid map of a wafer illustrating CD measurements taken in accordance with an aspect of the present invention.

FIG. 9 is a trimming measurement table correlating the CD measurements of FIG. 8 with desired values for the CDs in accordance with the present invention.

DETAILED DESCRIPTION OF THE INVENTION

Figure 1:
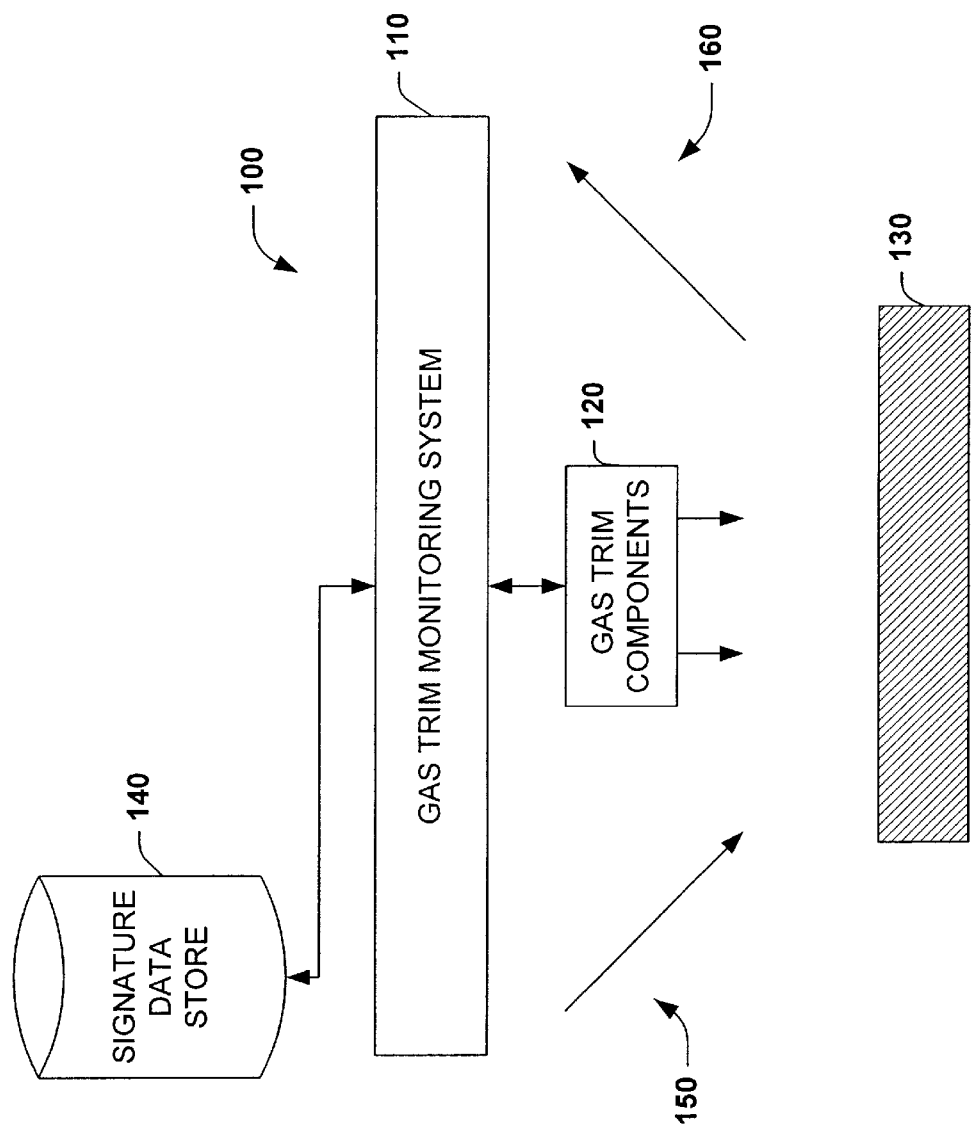
FIG. 1 is a schematic block diagram of a system for monitoring and controlling a gaseous phase chemical trim process in accordance with an aspect of the present invention.

The present invention is now described with reference to the drawings, wherein like reference numerals are used to refer to like elements throughout. In the following description, for purposes of explanation, numerous specific details are set forth in order to provide a thorough understanding of the present invention. It may be evident, however, to one skilled in the art that the present invention may be practiced without these specific details. In other instances, well-known structures and devices are shown in block diagram form in order to facilitate describing the present invention.

The term "component" refers to a computer-related entity, either hardware, a combination of hardware and software, software, or software in execution. For example, a component may be a process running on a processor, a processor, an object, an executable, a thread of execution, a program and a computer. By way of illustration, both an application running on a server and the server can be components. By way of further illustration, both an ion gun and a process controlling an ion gun can be components.

It is to be appreciated that various aspects of the present invention may employ technologies associated with facilitating unconstrained optimization and/or minimization of error costs. Thus, non-linear training systems/methodologies (e.g., back propagation, Bayesian, fuzzy sets, non-linear regression, or other neural networking paradigms including mixture of experts, cerebella model arithmetic computer (CMACS), radial basis functions, directed search networks and function link networks) may be employed.

Referring initially to FIG. 1, a system 100 for monitoring and controlling a gaseous phase chemical trim process is illustrated. Such chemical gaseous phase trim processes may be employed, for example, to reduce the size of features patterned into a photoresist. In gaseous phase chemical trim systems, a gas containing one or more trimming chemicals (e.g., acids, bases) are exposed to a patterned photoresist (e.g., in a reaction chamber). One example gaseous phase chemical trim process includes a method of trimming a patterned resist that involves the steps of providing the patterned resist having structural features of a first size, the patterned resist containing a polymer having a labile group; exposing the patterned photoresist to a gas containing at least one cleaving compound to form a thin deprotected resist layer at an interface between the patterned resist and the gas; and removing the gas and the thin deprotected resist layer leaving the patterned resist having structural features of a second size, wherein the second size is smaller than the first size. Another example gaseous phase chemical trim process includes a chemical trim process that involves the steps of forming a patterned resist, the patterned resist containing a polymer having an acid labile pendent group; exposing the patterned resist to a gas containing an acid, thereby forming a thin deprotected resist layer at an interface between the patterned resist and the acid containing gas; and removing the acid containing gas and the thin deprotected resist layer thereby providing a trimmed patterned resist. Yet another example chemical trim process includes a process involving the steps of forming a patterned resist, the patterned resist comprising a polymer having a base labile pendent group; exposing the patterned resist to a gas containing a base, thereby forming a thin deprotected resist layer at an interface between the patterned resist and the base containing gas; and removing the base containing gas and the thin deprotected resist layer thereby providing a trimmed patterned resist.

The trimming compounds may make a portion of the patterned photoresist soluble to a developer, for example, which facilitates creating smaller features in the patterned photoresist, which in turn facilitates creating smaller features in a layer (e.g., an oxide layer) under the patterned photoresist. The trim rate is generally proportional to the formulae of the trimming compound, the concentration of the trimming compound, the volume of the trimming compound, the vapor pressure inside a reaction chamber and/or the temperature inside the trim chamber. Thus, conventional techniques may employ indirect measurements, including attempts to reproduce gas exposure times, formulae, concentrations, pressures and/or temperatures that produced acceptable trimming on previous wafers, to determine trimming progress. Other conventional indirect techniques may include monitoring the gas evacuated from the reaction chamber to determine the amount of resist that has been trimmed away. Although the amount of resist that has been trimmed away can be employed to approximate when a trimming process is complete, such indirect monitoring does not provide feedback concerning any particular wafer and/or feature. Thus, such techniques do not provide direct information concerning CDs being achieved on a wafer 130 and do not account for wafer to wafer and/or feature to feature variations.

The system 100 includes a gas trim monitoring system 110 operative to direct a light 150 at a wafer 130 upon which there is a patterned photoresist that is going to be trimmed or that is in the process of being trimmed, for example. The gas trim monitoring system 110 can be a standalone device and/or can also be distributed between two or more cooperating devices and/or processes. The gas trim monitoring system 110 can reside in one physical or logical device (e.g., computer, process) and/or be distributed between two or more physical or logical devices. The gas trim monitoring system 110 may include one or more components that are located inside the trim chamber and/or one or more components that are not located inside the trim chamber. The gas trim components 120 may be employed, for example, in gaseous phase trimming techniques where the mechanism of trimming has a physical chemical basis.

In one example gaseous phase chemical trim process, a patterned resist is exposed to a gas containing a cleaving compound. While the resist is in contact with the gas containing a cleaving compound, a chemical interaction takes place within the portions of the resist adjacent the gas, forming a thin deprotected resist layer within the resist. Although not wishing to be bound by any theory, it is believed that the cleaving compound from the gas diffuses into a thin portion of the resist adjacent the coating. It is believed that cleaving compounds at or near the interface of the gas and the resist cause a chemical change wherein labile groups of the resist polymer are cleaved or deprotected and the cleaved or deprotected portions of the resist become removable by an appropriate solvent or developer. That is, the cleaving compound cleaves labile moieties of the resist material, thereby changing the solubility characteristics of the thin portion of the resist material wherein such cleavage takes place. Thus, a thin deprotected resist layer is formed within the developed resist which is then removable or further developable after or while the coating is removed. For example, an acid containing gas is introduced into a reaction chamber where a patterned acid catalyzed resist is located. While the resist is in contact with the acid containing gas, a chemical interaction takes place within the portions of the resist adjacent the acid containing gas forming a thin deprotected resist layer within the resist. Again, although not wishing to be bound by any theory, it is believed that hydronium ions or protons from the acid containing gas diffuse into a thin portion of the resist adjacent the acid containing gas. It is believed that hydronium ions or protons at or near the interface of the acid containing gas and the resist polymer cause a chemical change wherein the deprotected portions of the resist become removable by an appropriate developer. That is, hydronium ions or protons cleave acid labile moieties of the resist material, such as t-butoxycarbonyl moieties from a resist polymer backbone, thereby changing the solubility characteristics of that portion of the resist material. Thus, a thin deprotected resist layer is formed within the developed resist which is then removable after or while the acid containing gas is removed.

The light 150 may be generated by many different light sources, and in one example aspect of the present invention the light 150 is generated by a frequency-stabilized laser.

The gas trim monitoring system 110 may direct the light 150 at substantially all of the wafer 130 and/or at selected portions of the wafer. By way of illustration, in one example aspect of the present invention, the light 150 may be directed at selected portions of the wafer 130, where such portions provide data sufficient to generate scatterometry signatures. A light 160 reflected from the wafer 130 is collected by the gas trim monitoring system 110, which may then employ scatterometry techniques to analyze the reflected light 160 to determine one or more trim parameters associated with trimming the patterned photoresist located on the wafer 130. For example, the width of lines may be analyzed to determine whether acceptable critical dimensions have been achieved. Other parameters including, but not limited to horizontal trim rate, vertical trim rate and trim-rate percent uniformity may also be analyzed.

It is to be appreciated that the surface of the wafer 130, including features, can both reflect and refract the light 150, so that the light 160 can be a complex reflected and/or refracted light. The scatterometry analysis can include comparing one or more scatterometry signatures associated with the reflected light 160 to one or more scatterometry signatures stored in a signature data store 140. Such signatures may be generated, for example, by combining phase and intensity information associated with the reflected light 160. As trimming progresses, light reflecting from a wafer 130 may produce various signatures. The sequence in which such signatures are generated can be employed to determine the rate at which trimming is progressing. For example, at a first point in time T1, light reflected from the wafer 130 may produce a signature S1 that indicates that lines with a first width W1 have been produced. Similarly, at a second point in time T2, light reflected from the wafer 130 may produce a signature S2 that indicates that lines with a second width W2 have been produced and at a third point in time T3, light reflected from the wafer 130 may produce a signature S3 that indicates that lines with a third width W3 have been produced. Analyzing the sequence of signatures, and the time required to produce transitions between such signatures can facilitate determining whether trimming is progressing at an acceptable rate. Feedback information can be generated from such sequence analysis to maintain, increase and/or decrease the rate at which trimming progresses. For example, parameters including, but not limited to gas formulae, gas pressure, gas volume, gas temperature and reaction chamber temperature can be altered to affect the trimming rate based on the signature sequence analysis.

The signature data store 140 can store data in data structures including, but not limited to one or more lists, arrays, tables, databases, stacks, heaps, linked lists and data cubes. The signature data store 140 can reside on one physical device and/or may be distributed between two or more physical devices (e.g., disk drives, tape drives, memory units). Analyses associated with the reflected light 160 and/or the signatures stored in the signature data store 140 can be employed to control one or more gaseous phase chemical trimming components 120.

The precision with which patterned photoresist portions are removed to create fine line patterns on the patterned photoresist and the resulting precision in the distance between the remaining portions corresponds to the precision with which CDs are achieved. Therefore, the precision of the processing performed by the gas trim components 120 is directly related to the feature sizes and CDs that can be achieved on the wafer 130.

Figure 2:
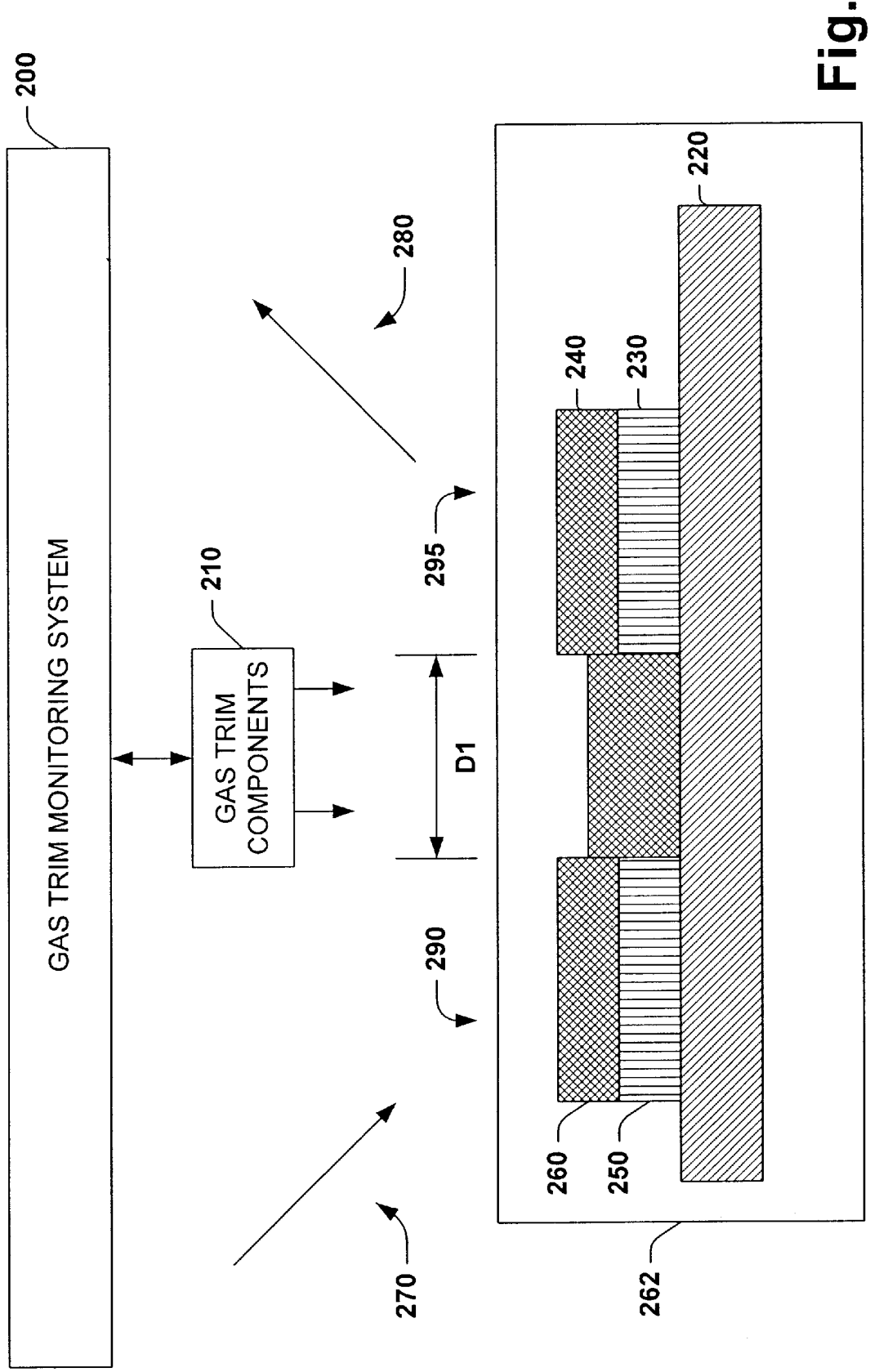
FIG. 2 is a cross-sectional view of a photoresist layer on a wafer being trimmed and monitored in accordance with an aspect of the present invention.

Turning now to FIG. 2, a gaseous phase chemical trim monitoring system 200 is illustrated directing a light 270 at a wafer 220 and receiving back a reflected light 280. The gaseous phase chemical trim monitoring system 200 can be a standalone device and/or can also be distributed between two or more cooperating devices and/or processes. The gaseous phase chemical trim monitoring system 200 can reside in one physical or logical device (e.g., computer, process) and/or be distributed between two or more physical or logical devices. The gaseous phase chemical trim monitoring system 200 may include one or more components that are located inside a trim chamber (not illustrated in FIG. 2) and/or one or more components that are not located inside a trim chamber.

The reflected light 280 will be affected by parameters including, but not limited to the chemical properties of the wafer 220 and/or the layers on the wafer 220, the size, shape and location of features on the wafer 220, the size, shape and location of gratings on the wafer 220 and the size, shape and location of spaces between such features. By way of illustration, a gap D1 between a first feature 290 and a second feature 295 is illustrated. The first feature 290 is illustrated as having an oxide layer 250 substantially covered by a hardened photoresist layer 260. Similarly, the second feature 295 is illustrated as having an oxide layer 230 substantially covered by a hardened photoresist layer 240. The features, the oxide layers and the patterned resist layers are illustrated as being substantially surrounded by a gas cloud 262. One or more gas chemical trimming components 210 are illustrated operatively connected to the gas trim monitoring system 200. The gas trim components 210, which may be one or more of a variety of gas trim components known in the art can be employed to introduce gas into a reaction chamber, to control process temperature, and the like, which in turn facilitates more precisely removing patterned photoresist. Thus, portions of the patterned photoresist 260 and 240 may be removed as a result of gaseous phase chemical trim processes associated with the gas trim components 210 and the gas 262.

The gap D1 and/or the geometry of the layers 230, 240, 250 and 260 and/or the relationships between the geometry of the layers 230, 240, 250 and 260 can be measured by the trim monitoring system 200 to determine whether desired CDs have been achieved on the wafer 220. For example, a signature associated with the gap D1 and the geometry of the layers 230, 240, 250 and 260 may indicate that further trimming of the layers 240 and 260 by the gas cloud 262 may be required. Such trimming may require, for example, additional chemical trimming compound, a different temperature, a different pressure and/or a change of formula. Thus, information operable to control the gas trim components 210 may be generated by the trim monitoring system.

As trimming of the patterned photoresist layers 240 and 260 progresses, light reflecting from the wafer 220, the patterned photoresist layers 240 and 260 and/or the features 290 and 295 may produce various signatures. The sequence in which such signatures are generated can be employed to determine the rate at which trimming is progressing. Similarly, the sequence of such signatures may be employed to determine the rate at which the gap D1 is changing. Such changes in rates can be employed to determine completion times, for example, and thus can be employed to facilitate scheduling subsequent gaseous phase chemical trim processes.

By way of illustration, at a first point in time T5, light reflected from the wafer 220, the patterned photoresist layers 240 and 260 and/or the features 290 and 295 may produce a signature S5 that indicates that the gap D1 has reached a first measurement. Similarly, at a second point in time T6, light reflected from the wafer 220, the patterned photoresist layers 240 and 260 and/or the features 290 and 295 may produce a signature S6 that indicates that the gap D1 has reached a second measurement and at a third point in time T7, light reflected from the wafer 220, the patterned photoresist layers 240 and 260 and/or the features 290 and 295 may produce a signature S6 that indicates that the gap D1 has reached a third desired measurement, and that trimming should conclude. Analyzing the sequence of signatures, and the time required to produce transitions between such signatures can facilitate determining whether trimming is progressing at an acceptable rate. Feedback information can be generated from such sequence analysis to maintain, increase and/or decrease the rate at which trimming progresses by, for example, manipulating gas formulae, trim chamber temperature, etc.

Figure 3:
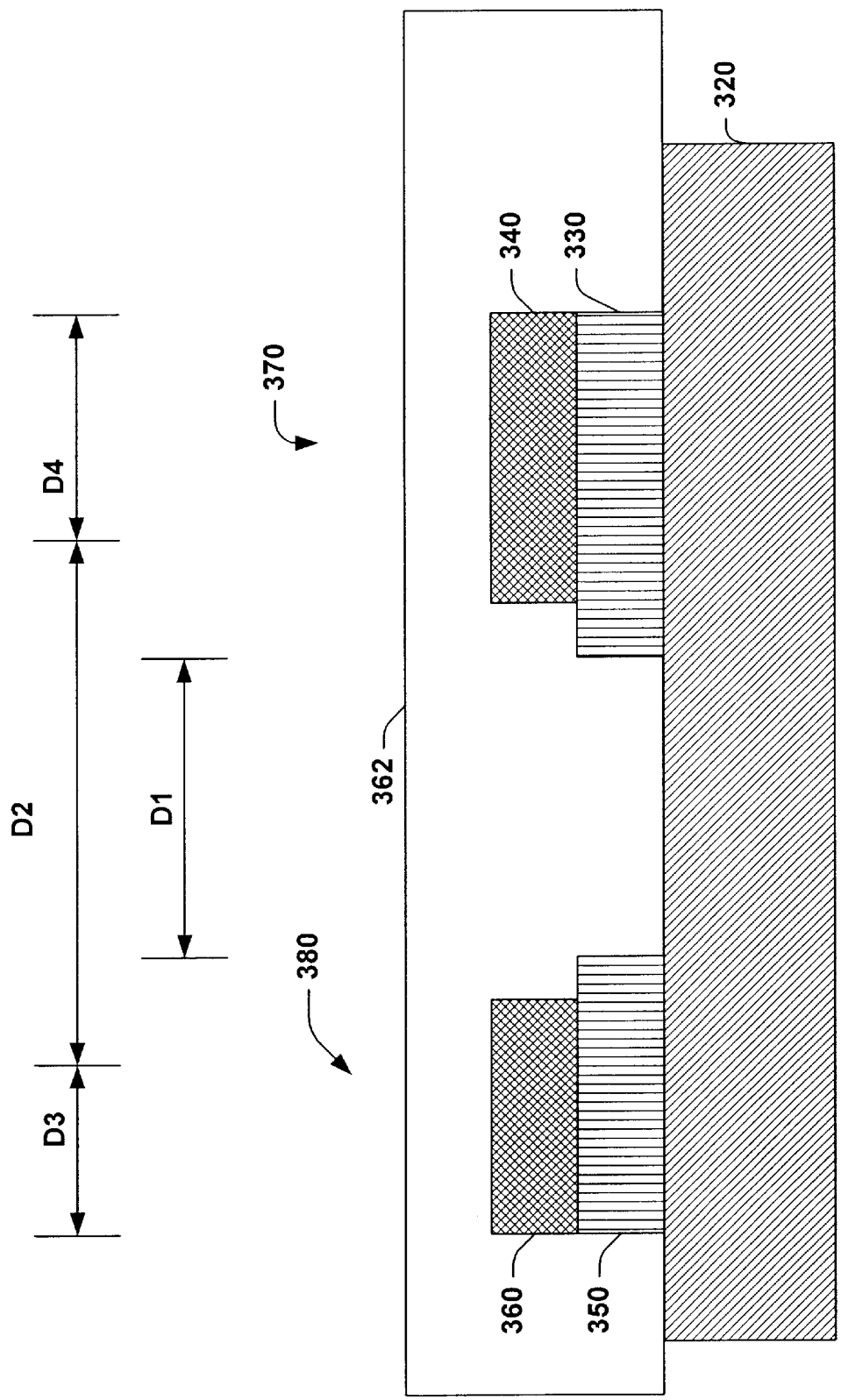
FIG. 3 is a cross-sectional view of a wafer being monitored for CDs in accordance with an aspect of the present invention.

Turning now to FIG. 3, measurements that may affect signatures generated by a scatterometry system associated with controlling one or more gaseous phase chemical trim processes to facilitate achieving desired critical dimensions are illustrated. Controlling such measurements (e.g, gate width and thickness, linewidth and thickness) can be important to reliable and efficient operation of an integrated circuit. For example, both gate delay and drive current are proportional to the inverse of the gate length. Thus, gate lengths should be tightly controlled across chips and wafers to facilitate correlating and sequencing signals. A wafer 320 is illustrated with two features 370 and 380. The feature 370 is illustrated with an oxide layer 330 and a hardened photoresist layer 340. Similarly, the feature 380 is illustrated with an oxide layer 350 and a hardened photoresist layer 360. While the oxide layers 350 and 330 are separated by a distance D1, this distance may, for example, be too small for reliable operation of the integrated circuit being fabricated on the wafer 320 or to allow for the creation of a subsequent intervening feature in the gap measured by D1.

A desired critical dimension for the distance between the oxide layer 350 and the oxide layer 330 may be the distance D2. For example, a gap of size D2 may be required to facilitate fabricating a subsequent feature that will reside between the features 370 and 380. Lithography sufficient to harden the photoresist layer 360 and the photoresist layer 340 may have occurred at an earlier point in time, but the lithography may have produced the layers 360 and 340 in such a manner that they will not produce the desired CD (e.g., gap size D2). Thus, the gas 362 may be exposed to the patterned photoresist layers 360 and 340, in an attempt to reduce the size of the patterned photoresist layers to widths D3 and D4, which would then allow the gap size D1 to be increased to the gap size D2. It is to be appreciated that the gas 362 may be introduced into a reaction chamber under varying conditions (e.g., temperatures, pressures, volumes). In one example of the present invention, the gas 362 is periodically evacuated from the reaction chamber so that the light employed in the scatterometry analysis is substantially unaffected by the gas 362.

Thus, the present invention facilitates generating information concerning the distances D1, D2, D3 and D4 and the resulting topographies of resist and oxide layers. Such information, generated, at least in part, in response to in-situ reflected light being analyzed by scatterometry techniques can be employed to provide real-time feedforward information that can be employed to control gaseous phase chemical trim processes so that desired critical dimensions can be achieved, thus providing advantages over conventional systems. For example, one or more signatures associated with the wafer 320, the patterned photoresist layers 360 and 340 and/or the features 370 and 380 can be generated. At a first point in time T11, a signature S10 may be generated that indicates that desired critical dimensions have not been achieved. Thus, a trimming process may be adapted in an attempt to achieve the desired critical dimension. For example, parameters including temperature, pressure, volume, and gas formula may be adapted. Then, at a second point in time T11, a signature S11 may be generated that indicates that although the desired critical dimensions have still not been achieved, that progress toward the desired critical dimension has occurred. Thus, the trimming process may be continued until a later point in time T12, when a signature S12 indicates that the desired critical dimensions have been achieved. However, the signature S11 may have indicated that the adaptation to the trimming process produced a movement away from desired critical dimensions, and thus all or portions of the wafer 320 may need to be marked for rejection or further adaptations of the chemical trim process may be attempted.

Figure 4:
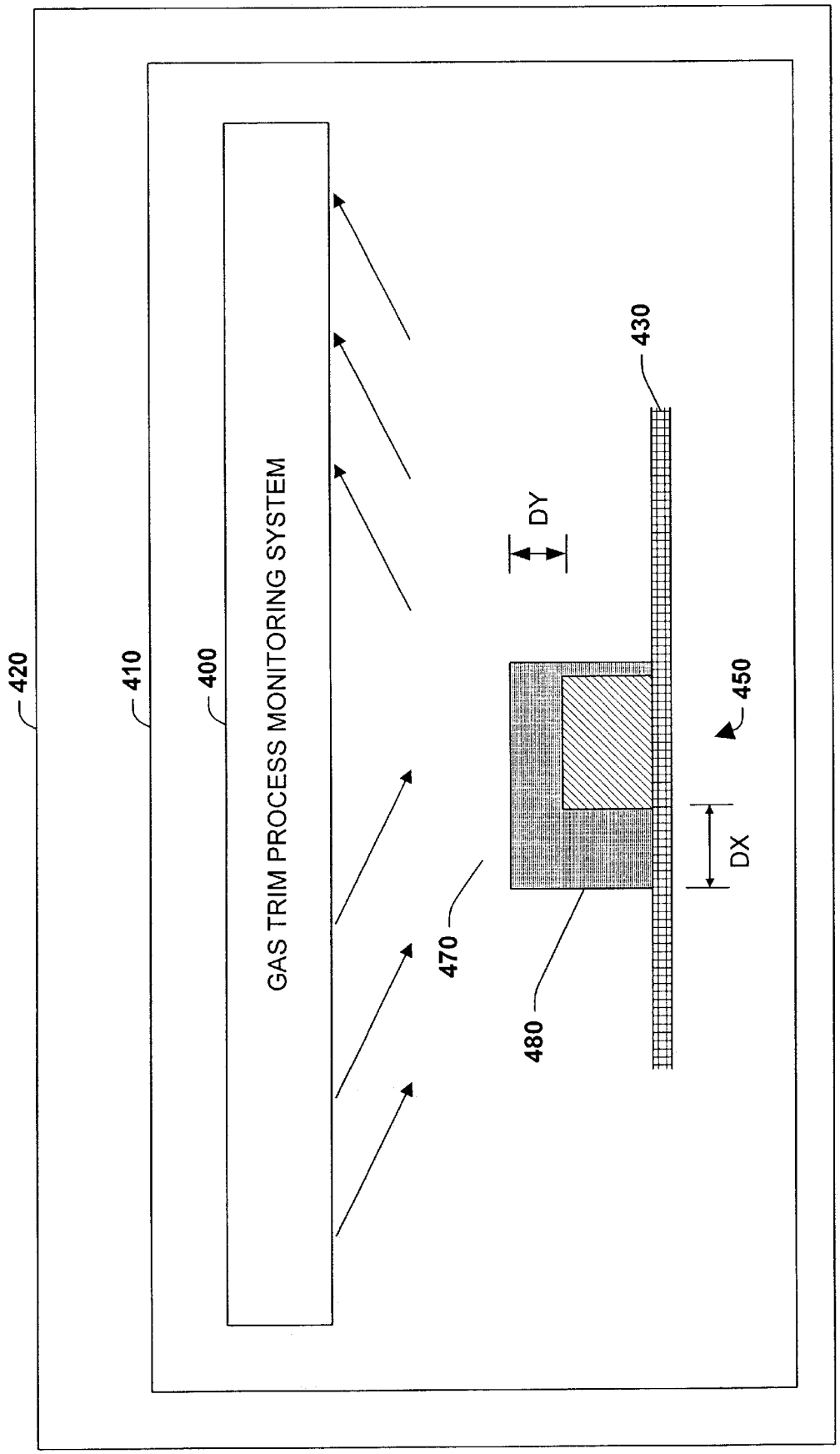
FIG. 4 is a cross-sectional view of a wafer being trimmed and monitored in accordance with an aspect of the present invention.

Thus, turning to FIG. 4, a gaseous phase chemical trim process monitoring system 400 is illustrated monitoring the chemical trimming being performed by a chemical trim gas 410 to which the wafer 430 has been exposed, whereupon a patterned photoresist layer 480 applied on a feature 450 is being trimmed to facilitate producing desired CDs for the feature 450. While a feature 450 is illustrated, it is to be appreciated that gratings may also be analyzed in accordance with the present invention. The gaseous phase chemical trim process facilitated by the gas 410 can be monitored by the gaseous phase chemical trim process monitoring system 400 until, for example, signatures indicating that desired reductions DX and DY are achieved. At such time, the chemical trim process facilitated by the gas 410 can be terminated, and subsequent processing can proceed. Retrieving in-situ information concerning direct measurements of the reductions DX and DY, and/or similar information from one or more gratings, and producing real-time feed-forward information that can be employed to adapt the chemical trim process facilitated by the gas 410 and/or other chemical trim processes, facilitates achieving more precise CDs and thus provides advantages over conventional systems. By way of illustration, conventional laser reflectance monitoring methods do not provide in-situ trim rate information. By way of further illustration, in laser interferometry methods, the laser must be focused on an open flat region, thus prime wafer real estate is sacrificed for the testing area. Also, such laser interferometry methods may only provide information on a limited area of the wafer surface. Furthermore, conventional systems that monitor gas evacuated from a reaction chamber do not provide information concerning any individual feature or CD, and thus the present invention, which can provide such individualized feedback provides advantages over such conventional systems.

In one example of the present invention, the gas trim process monitoring system 400 is located inside a process chamber 420, wherein the gas 410 is introduced to trim the wafer 430. In another example of the present invention, the gas 410 is periodically evacuated from the process chamber 420 so that the light employed in the scatterometry processing is not affected by the gas 410.

During the monitoring of the trimming of the patterned photoresist layer 480, it may be determined that the reduction DY is occurring more quickly than the reduction DX, thus, the trim process may be altered to affect the relative trim rates associated with the reductions DY and DX, to facilitate achieving desired CDs.

The time during which the gas 410 is permitted to contact the resist 480 may depend, for example, upon the identity of the gas 410, the concentration of the cleaving compound in the gas 410, the identity of the resist 480, the pressure inside the reaction chamber 420, the temperature inside the reaction chamber 420 and the desired size of the thin deprotected resist layer. In one example, the gas 410 is permitted to contact the resist 480 for a time period from about 1 second to about 3 hours, although slightly shorter or longer times may be permitted. In another example, the gas 410 is permitted to contact the resist 480 for a time period from about 10 seconds to about 30 minutes. In yet another example, the gas 410 is permitted to contact the resist 480 for a time period from about 15 seconds to about 5 minutes. Generally, a longer contact time leads to a thicker resulting thin deprotected resist layer. Thus, the present invention facilitates determining an appropriate time for the gas 410 to be in contact with the resist 480, and, in one example, the feed-forward control information facilitates terminating the contact period, and thus the present invention provides improvements over conventional systems that employ preprogrammed contact times.

Optionally, heat is applied when the gas 410 is brought in contact with the resist 480. In some instances, heat promotes the formation of the thin deprotection layer. In one example, the gas 410 is contacted with the resist 480 at a temperature from about 20° C. to about 200°C. In another example, the gas 410 is contacted with the resist 480 at a temperature from about 40° C. to about 150° C. In yet another example, the gas 410 is contacted with the resist 480 at a temperature from about 50° C. to about 110° C. In some examples where the gas contains an acid, heat particularly promotes the formation of the thin deprotection layer. Thus, the present invention facilitates monitoring the results of the trim process and further facilitates adapting the trim process by, for example, changing the temperature in the trim chamber.

The pressure at which the gas 410 is maintained inside the reaction chamber 420 can impact the rate at which the gaseous phase trimming occurs. Thus, the present invention facilitates adapting the pressure inside the reaction chamber 420 based on in-situ feed-forward control information from the gas trim process monitoring system 400.

Figure 5:
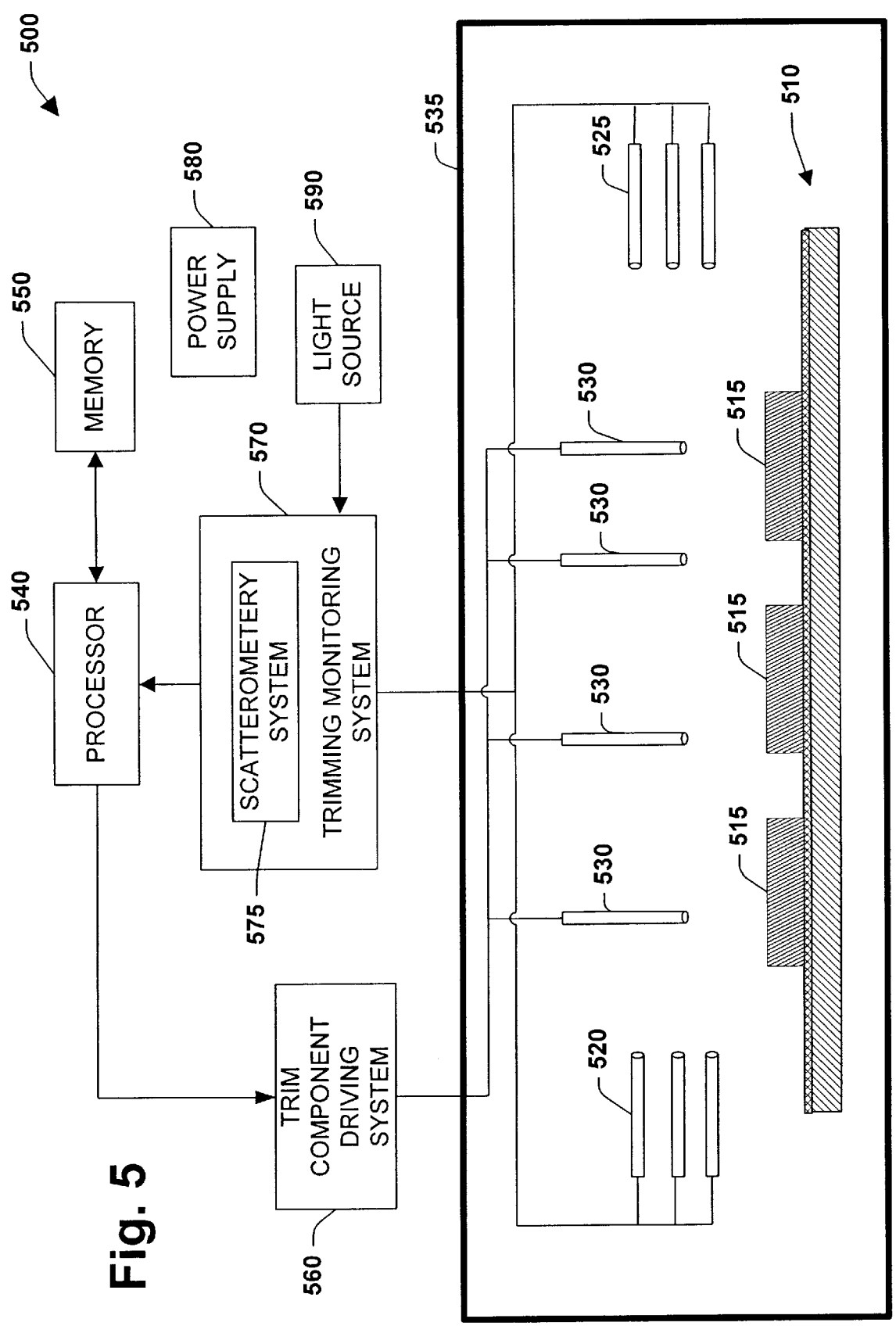
FIG. 5 is schematic block diagram of a trimming process CD monitoring and controlling system in accordance with an aspect of the present invention.

FIG. 5 illustrates a system 500 for monitoring and controlling gaseous phase chemical trim processes. The system 500 operates to control one or more trim components 530 in order to optimize gaseous phase chemical trim processes and to mitigate fabricating poorly trimmed features and wafers. A trimming monitoring system 570, a processor 540 and a trim component driving system 560 work cooperatively to control the trim components 530. In one example of the present invention, the trim components 530 are contained within a process chamber 535, wherein a gas will be employed to trim the patterned resist.

The trim components 530 are coupled to and controlled directly by the trim component driving system 560. The trim component driving system 560 receives information and/or instructional commands from the processor 540. The processor 540 determines the content and type of information transmitted to the trim component driving system 560 according to its analysis of data received from and collected by the monitoring system 570. Thus, through the interaction of components 530, 570, 540 and 560, the system 500 has the ability to improve subsequent chemical trim processes for the same wafer and/or for subsequent wafers. For example, changes to gas concentration, reaction chamber 535 temperature, reaction chamber 535 pressure and the like in response to in-situ feed-forward control information from the process 540 are possible, providing advantages over conventional systems. Such interaction between the components 530, 570, 540 and 560 also facilitates customizing a chemical trim process to wafers with different densities of features, providing an improvement over conventional systems. In addition, by communicating measurements relating to recently trimmed features/wafers to the processor 540, the processor 540 can control the chemical trimming component driving system 560, which can thus regulate the one or more chemical trimming components 530 to facilitate obtaining more precise and improved chemical trim processes. In one example of the present invention, such control may be adapted over time by various machine learning techniques. Thus trimming errors can be mitigated and higher packing densities and smaller feature sizes can be achieved through the optimizations achieved through such machine learned adaptations.

The system 500 includes one or more chemical trimming components 530 that are selectively controlled to facilitate controlled trimming of the wafer 510. One or more target light sources 520 project light onto respective portions of the wafer 510. A portion of the wafer 510 may have one or more gratings 515 and/or features located on that portion. Light reflected and/or refracted by the one or more gratings 515 is collected by one or more light detecting components 525, and processed by a trimming monitoring system 570 to measure at least one parameter relating to the trimming of one or more features and/or the one or more gratings 515. For example, spaces between portions of the grating 515 and spaces between the gratings 515 can be measured and compared to desired critical dimensions (CDs). The reflected light is measured with respect to the incident light in order to obtain the various parameters relating to the gratings 515.

The monitoring system 570 includes a scatterometry system 575. It is to be appreciated that any suitable scatterometry system may be employed to carry out the present invention, and such systems are intended to fall within the scope of the claims appended hereto.

A light source 590 (e.g., a laser) provides light to the one or more target light sources 520 via the monitoring system 570. Preferably, the light source 590 is a frequency-stabilized laser, however, it will be appreciated that any laser or other light source (e.g., laser diode or helium neon (HeNe) gas laser) suitable for carrying out the present invention may be employed. One or more light detecting components 525 (e.g., photo detector, photo diodes) collect light reflecting from the one or more gratings 515 and/or the one or more patterned photoresist layers being trimmed. The monitoring system 570 may also process the measured light data into a data form compatible with or understandable to the processor 540.

The processor 540 is operatively coupled to the monitoring system 570 and receives the measured trim parameter data from the monitoring system 570. The processor 540 determines the acceptability and/or progress of the trimming of the respective portions of the wafer 510 by examining measured CDs and comparing such measured CD values to stored acceptable and unacceptable CD values. The CD values may be associated with one or more signatures stored, for example, in a memory 550. In determining the acceptability and/or progress of an on-going and/or recently completed gaseous phase chemical trim process, the processor 540 may also determine to what extent, if any, adjustments to the chemical trimming components 530 and/or chemical trimming compounds are necessary to optimize subsequent chemical trim processes. Upon making the determination, the processor 540 transmits this information to the trim component driving system 560, which then makes one or more adjustments to the chemical trimming components 530 and/or chemical trimming compounds.

As described above, the processor 540 is also coupled to the chemical trimming component driving system 560 that directs and controls the one or more chemical trimming components 530. The chemical trimming component driving system 560 is controlled, at least in part, by the processor 540 to selectively vary the operation of the respective chemical trimming components 530. Each respective portion of the wafer 510 is associated with a corresponding chemical trimming component 530. The processor 540 monitors the trimming of one or more features and/or one or more gratings 515, and selectively regulates the trimming of each portion via the corresponding chemical trimming components 530. The transmission and relay of information between the monitoring system 570, the processor 540, the trim component driving system 560 and the trim components 530 creates effective feed back control that facilitates improving IC quality by producing more precisely trimmed patterned photoresists which in turn facilitates producing more precisely sized and/or shaped features.

The processor 540, or central processing unit, may be any of a plurality of commercially available processors. The processor 540 is programmed to control and operate the various components within the system 500 in order to carry out the various functions described herein. The manner in which the processor 540 is programmed to carry out the functions relating to the present invention will be apparent to those having ordinary skill in the art based on the description provided herein.

A memory 550, which is operatively coupled to the processor 540, is also included in the system 500 and serves to store, among other things, program code executed by the processor 540 for carrying out operating functions of the system 500 as described herein. For example, the memory 550 can hold patterns to which observed data can be compared. The memory 550 also serves as a storage medium for temporarily storing trim parameter data such as trimming progress values, trimming progress tables, component coordinate tables, grating sizes, grating shapes, scatterometry information, achieved CDs, desired CDs and other data that may be employed in carrying out the present invention.

A power supply 580 provides operating power to the system 500. Any suitable power supply (e.g., battery, line power) may be employed to carry out the present invention.

Figure 6:
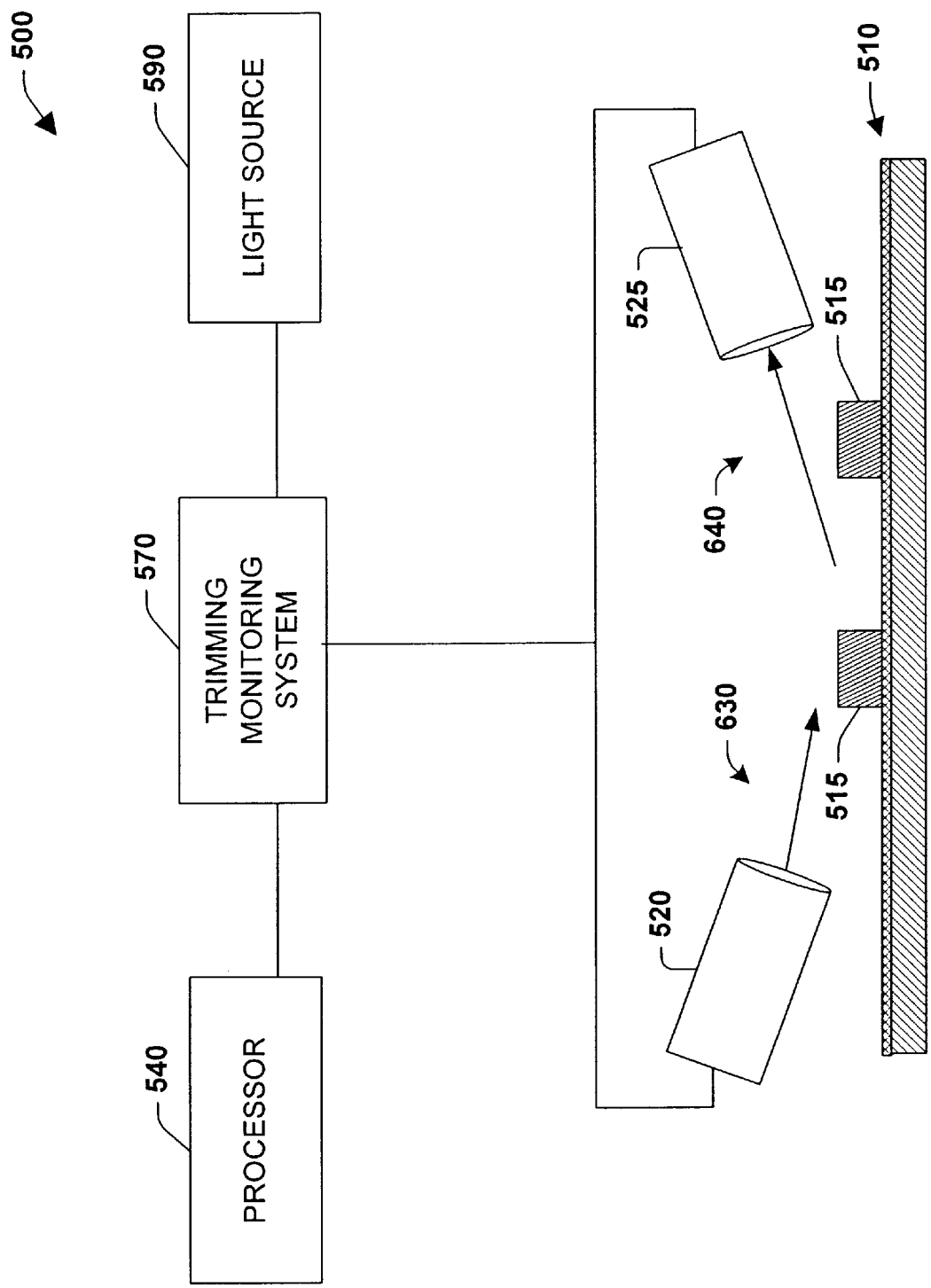
FIG. 6 is a partial schematic block diagram of the system of FIG. 5 being employed in connection with determining trimming progress by measuring grating CDs in accordance with an aspect of present invention.

Turning now to FIG. 6, one aspect of the present invention is shown. FIG. 6 illustrates the system 500 being employed to measure the trimming of a particular portion of the wafer 510. The target light source 520 directs a light 630 incident to the surface of the wafer 510. The angle of a light 640 reflected from the surface of the wafer 510 will vary in accordance with the evolving dimensions of a grating 515, and/or with the evolving characteristics (e.g., thickness, planarity) of one or more patterned photoresist layers being trimmed on the wafer 510. The one or more light detecting components 525 collect the reflected light 640 and transmit the collected light, and/or data associated with the collected light, to the monitoring system 570.

The monitoring system 570 collects the reflected light 640, and/or related data, in accordance with scatterometry techniques. The monitoring system 570 then provides the processor 540 with the data corresponding to the trimming characteristics associated with the wafer 510. The data may include, for example, information relating to the dimensions of trimmed areas relative to, or independent of, dimensions of untrimmed areas, and/or surface characteristics as well as other measurements relating to the chemical trim process.

In another aspect of the invention, the data may also include conclusory information including, but not limited to, whether desired dimensions have been reached and whether trimming should continue, whether desired CDs have been reached and thus whether adjustments are required and whether measured trim dimensions are within a pre-determined range.

The monitoring system 570 provides direct, real-time measurements to the processor 540, as opposed to measurements taken according to pre-determined system schedules and measurements taken post-fabrication. Providing direct, real-time feedback to the processor 540 facilitates selective control of chemical trim processes and improved trimming precision over conventional methods and/or apparatus. For example, reaction chamber temperature, pressure, and gas formulae may be adapted in real time to achieve more optimal trimming.

Turning now to FIGS. 7–9, another aspect of the present invention is shown. In addition to the methods described above, a wafer 710 may be logically partitioned into grid blocks to facilitate determining positions or locations where the wafer 710 may benefit from adjusting one or more chemical trim processes. Obtaining such positions or locations may facilitate determining to what extent, if any, chemical trim process parameter adjustments are necessary. Obtaining such information may also assist in determining problem areas associated with chemical trim processes.

FIG. 7 illustrates a perspective view of a chuck 730 supporting the wafer 710, whereupon one or more gratings may be formed. The wafer 710 may be divided into a grid pattern as shown in FIG. 8. Each grid block (XY) of the grid pattern corresponds to a particular portion of the wafer 710, and each grid block is associated with one or more gratings and/or one or more portions of one or more gratings. The grid blocks are individually monitored for chemical trim process parameters and trimming may be individually controlled for each grid block. It is to be appreciated that the size and/or shape of gratings can be manipulated to facilitate analyzing different critical dimensions. For example, for a particular layer in an integrated circuit, a CD relating to a width between features may be important. Thus, the gratings can be patterned to optimize analyzing the width between features.

In FIG. 8, one or more gratings in the respective portions of the wafer 710 ($X_1Y_1 \ldots X_{12}, Y_{12}$) are monitored for CDs produced during the chemical trim process using reflected light, the monitoring system 570 (FIG. 5) and the processor 540 (FIG. 5). Exemplary CD measurements produced during trimming for each grating are shown. As can be seen, the CD measurement at coordinate $X_7Y_6$ is substantially higher than the CD measurement of the other portions XY. It is to be appreciated that the wafer 710 may be mapped into any suitable number of grid blocks, and any suitable number of gratings may formed on the wafer 710. Although the present invention is described with respect to one chemical trimming component 530 corresponding to one grid block XY, it is to be appreciated that any suitable number of chemical trimming components 530 corresponding to any suitable number of wafer portions/grid blocks may be employed.

FIG. 9 is a representative table of CD measurements taken for the various grid blocks that have been correlated with acceptable CD values for the portions of the wafer 710 mapped by the respective grid blocks. As can be seen, all the grid blocks, except grid block $X_7Y_6$, have CD measurements corresponding to an acceptable CD table value (TA) (e.g., are within an expected range of trimming measurements), while grid block $X_7Y_6$ has an undesired CD table value (Tu). Thus, the processor 540 has determined that an undesirable trimming condition exists at the portion of the wafer 710 mapped by grid block $X_7Y_6$. Accordingly, the processor 540 can drive at least a chemical trimming component $530_{7,6}$, which corresponds to the portion of the wafer 710 mapped at grid block $X_7Y_6$, to attempt to produce an acceptable CD. It is to be appreciated that the chemical trimming components 530 may be driven so as to maintain, increase, and/or decrease, the rate of trimming of the respective portions of the wafer 710 as desired. In one example of the present invention, the chemical trimming component 530 associated with grid block $X_7Y_6$ may change the temperature associated with the grid block and/or the concentration of the active ingredients of a cleaving compound (e.g., acid, base, organic compound) associated with the grid block. When the processor 540 determines that the trimming process has reached a pre-determined threshold level, the processor 540 may terminate the trimming by one or more chemical trimming components 530, thus enabling more precise control of the trimming process, which provides advantages over conventional systems.

Figure 10:
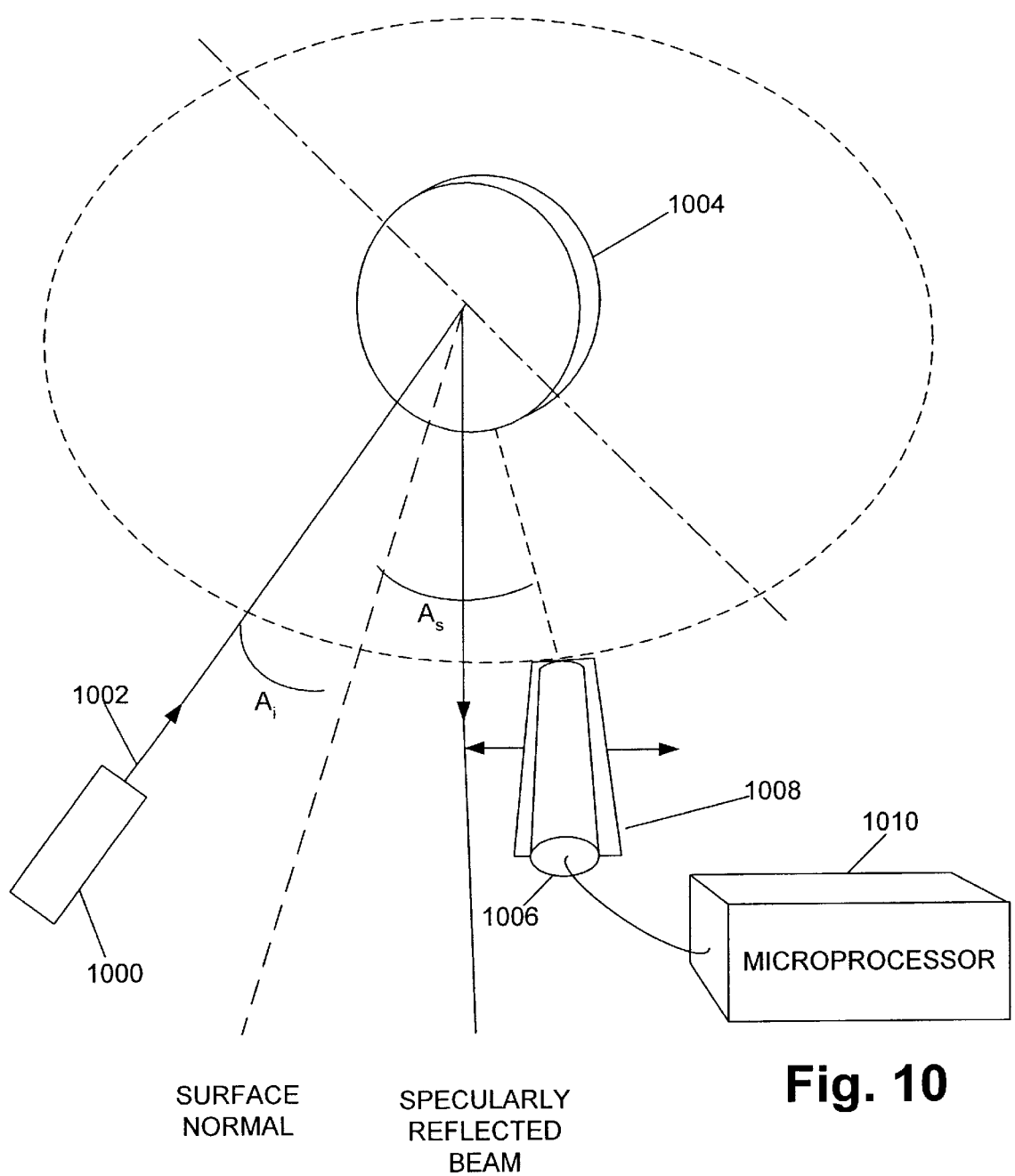
FIG. 10 illustrates an exemplary scatterometry system collecting reflected light.

FIG. 10 illustrates an exemplary scatterometry system collecting reflected light. Light from a laser 1000 is brought to focus in any suitable well-known manner to form a beam 1002. A sample, such as a wafer 1004, is placed in the path of the beam 1002 and a photo detector or photo multiplier 1006 of any suitable well-known construction. Different detector methods may be employed to determine the scattered power. To obtain a grating pitch, the photo detector or photo multiplier 1006 may be mounted on a rotation stage 1008 of any suitable well-known design. A microprocessor 1010, of any suitable well-known design, may be used to process detector readouts, including, but not limited to, angular locations of different diffracted orders leading to diffraction grating pitches being calculated. Thus, light reflected from the sample 1004 may be accurately measured.

Figure 11:
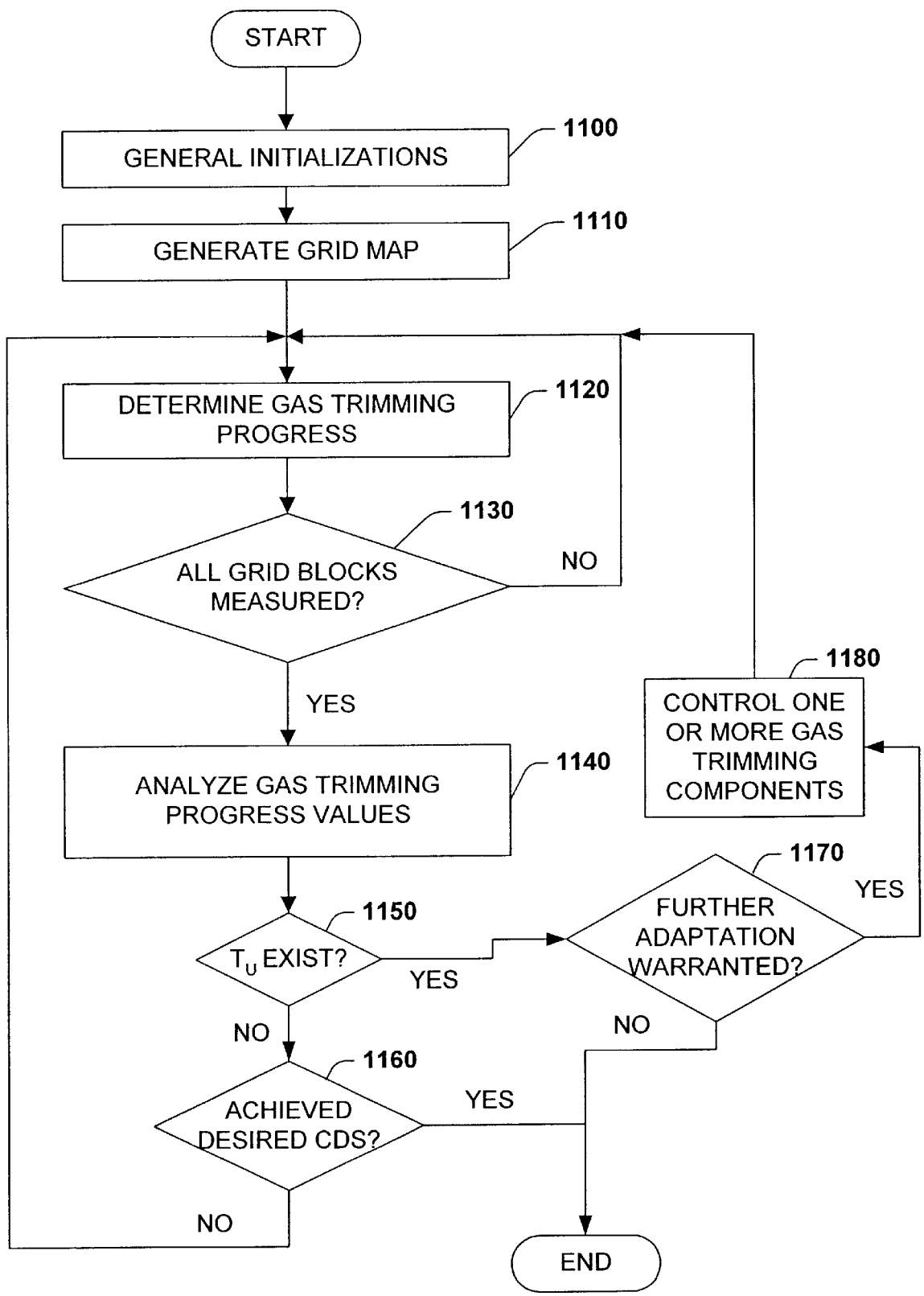
FIG. 11 is a flow diagram illustrating one specific methodology for carrying out the present invention.

In view of the exemplary systems shown and described above, methodologies that may be implemented in accordance with the present invention will be better appreciated with reference to the flow diagram of FIG. 11. While for purposes of simplicity of explanation, the methodology of FIG. 11 is shown and described as a series of blocks, it is to be understood and appreciated that the present invention is not limited by the order of the blocks, as some blocks may, in accordance with the present invention, occur in different orders and/or concurrently with other blocks from that shown and described herein. Moreover, not all illustrated blocks may be required to implement a methodology in accordance with the present invention.

FIG. 11 is a flow diagram illustrating one particular methodology for carrying out the present invention. At 1100, general initializations are performed. Such initializations can include, but are not limited to, establishing pointers, allocating memory, setting variables and establishing communication channels. At 1110, a grid map of a plurality of grid blocks "XY" is created. At 1120, trimming determinations are made with respect to the various wafer portions mapped by the respective grid blocks XY. At 1130, a determination is made concerning whether all grid block measurements have been taken. If the determination at 1130 is NO, then processing returns to 1120. If the determination at 1130 is YES, then at 1140, determined dimension values are analyzed and compared against acceptable CDs for the respective portions of a wafer. In an alternative example of the present invention, the determination at 1130 may concern whether a sufficient number of grid blocks have been measured to facilitate valid CD analysis.

At 1150, a determination is made concerning whether trimming values are not acceptable. If trimming values are acceptable, then processing continues at 1160 where a determination is made concerning whether desired CDs have been achieved. If desired CDs have been achieved, then processing can conclude. Otherwise, processing continues at 1120. If unacceptable dimension values are found at 1150, processing proceeds to 1170 where a determination is made concerning whether further adaptation is warranted. By way of illustration, the unacceptable dimension values may indicate that portions of the wafer and/or the entire wafer being processed have been damaged to such an extent that further adaptations to the chemical trim process are unwarranted. Such a damaged portion and/or wafer may be marked for rejection. By way of further illustration, analysis of the unacceptable dimensions may indicate that a simple adaptation is appropriate. After the analyses, relevant chemical trimming components corresponding to grid blocks with unacceptable trimming values are controlled to regulate the trimming of the respective wafer portions to facilitate achieving desired dimensions. For example, parameters including, but not limited to temperature, compound formulae and reaction time may be adjusted. The present iteration is then ended and the process returns to 1120 to perform another iteration.

Turning now to FIGS. 12–17, a concept of scatterometry and how it is employed in the present invention is discussed. Scatterometry is a technique for extracting information about a surface upon which an incident light has been directed. Scatterometry is a metrology that relates the geometry of a sample to its scattering effects. Scatterometry is based on the reconstruction of a grating profile from its optical diffraction responses. Information concerning properties including, but not limited to, dishing, erosion, profile, planarity, thickness of surfaces and critical dimensions of features present on the surface can be extracted. The information can be extracted by comparing the phase and/or intensity of a light directed onto the surface with phase and/or intensity signals of a complex reflected and/or diffracted light resulting from the incident light reflecting from and/or being diffracted by the surface upon which the incident light was directed. The intensity and/or the phase of the reflected and/or diffracted light will change based on properties of the surface upon which the light is directed. Such properties include, but are not limited to, the chemical properties of the surface, the planarity of the surface, features on the surface, voids in the surface, and the number and/or type of layers beneath the surface. In the present invention, the intensity and/or phase of the reflected and/or diffracted light will be examined as it relates to critical dimensions desired on the wafer being trimmed.

Different combinations of the above-mentioned properties will have different effects on the phase and/or intensity of the incident light resulting in substantially unique intensity/phase signatures in the complex reflected and/or diffracted light. Thus, by examining a signal (signature or stored value) library of intensity/phase signatures, a determination can be made concerning the properties of the surface. Such substantially unique phase/intensity signatures are produced by light reflected from and/or refracted by different surfaces due, at least in part, to the complex index of refraction of the surface onto which the light is directed. The complex index of refraction (N) can be computed by examining the index of refraction (n) of the surface and an extinction coefficient (k). One such computation of the complex index of refraction can be described by the equation:

$N = n - jk$, where $j$ is an imaginary number.

The signal (signature) library can be constructed from observed intensity/phase signatures and/or signatures generated by modeling and simulation. By way of illustration, when exposed to a first incident light of known intensity, wavelength and phase, a first feature on a wafer can generate a first phase/intensity signature. Similarly, when exposed to the first incident light of known intensity, wavelength and phase, a second feature on a wafer can generate a second phase/intensity signature. For example, a line of a first width may generate a first signature while a line of a second width may generate a second signature. Observed signatures can be combined with simulated and modeled signatures to form the signal (signature) library. Simulation and modeling can be employed to produce signatures against which measured phase/intensity signatures can be matched. In one exemplary aspect of the present invention, simulation, modeling and observed signatures are stored in a signal (signature) library containing over three hundred thousand phase/intensity signatures. Thus, when the phase/intensity signals are received from scatterometry detecting components, the phase/intensity signals can be pattern matched, for example, to the library of signals to determine whether the signals correspond to a stored signature.

Figure 12:
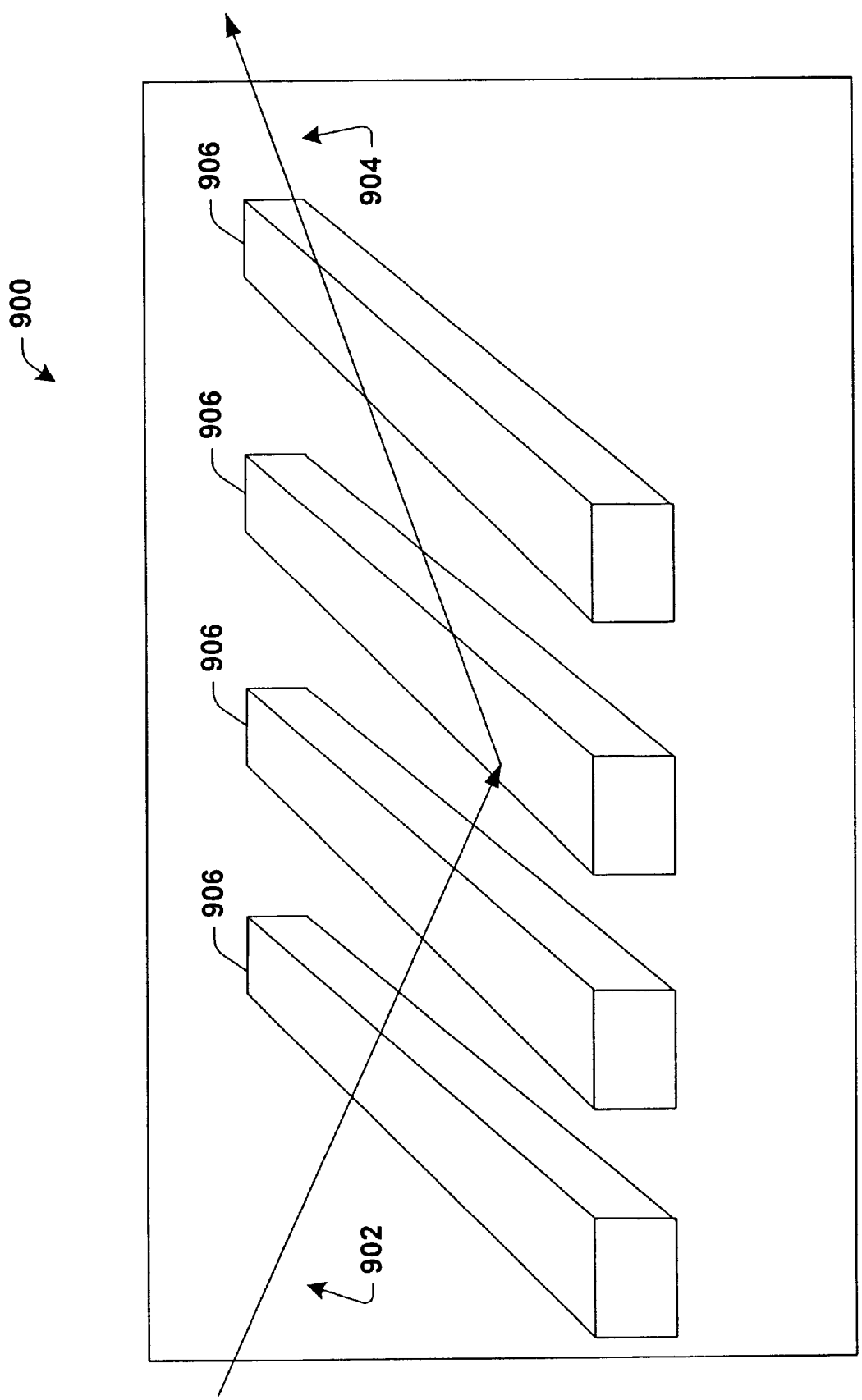
FIG. 12 is a simplified perspective view of an incident light reflecting off a surface, in accordance with an aspect of the present invention.

To illustrate the principles described above, reference is now made to FIGS. 12 through 17. Referring initially to FIG. 12, an incident light 902 is directed at a surface 900, upon which one or more features 906 may exist. The incident light 902 is reflected as reflected light 904. The properties of the surface 900, including but not limited to, thickness, uniformity, planarity, chemical composition and the presence of features, can affect the reflected light 904. The features 906 are raised upon the surface 900. The phase and intensity of the reflected light 904 can be measured and plotted, as shown, for example, in FIG. 17. The phase 960 of the reflected light 904 can be plotted, as can the intensity 962 of the reflected light 904. Such plots can be employed to compare measured signals with signatures stored in a signature library using techniques like pattern matching, for example.

Figure 13:
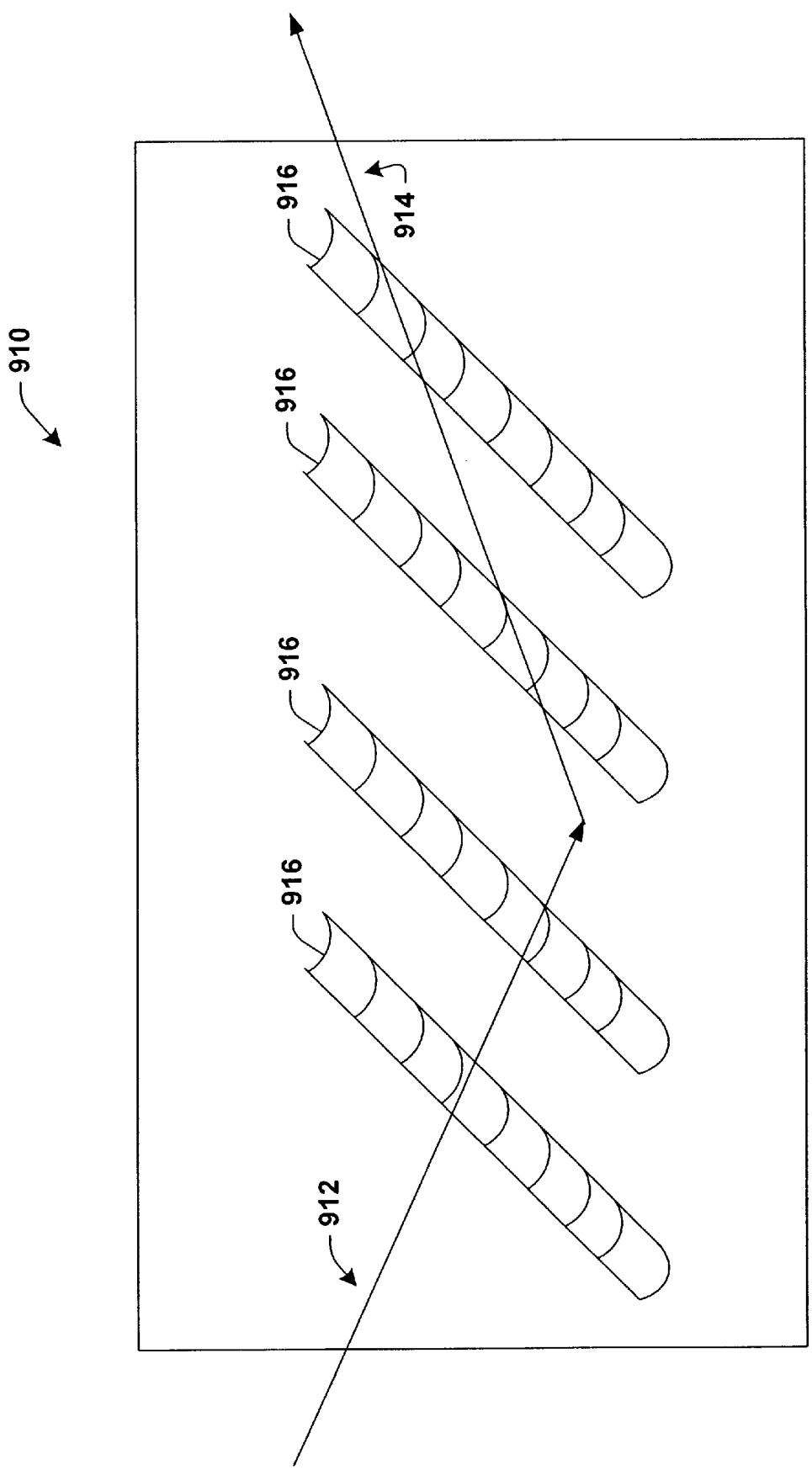
FIG. 13 is a simplified perspective view of an incident light reflecting off a surface, in accordance with an aspect of the present invention.

Referring now to FIG. 13, an incident light 912 is directed onto a surface 910 upon which one or more depressions 916 appear. The incident light 912 is reflected as reflected light 914. Like the one or more features 906 (FIG. 12) may affect an incident beam, so too may the one or more depressions 916 affect an incident beam. Thus, it is to be appreciated that scatterometry can be employed to measure features appearing on a surface, features appearing in a surface, and properties of a surface itself, regardless of features.

Figure 14:
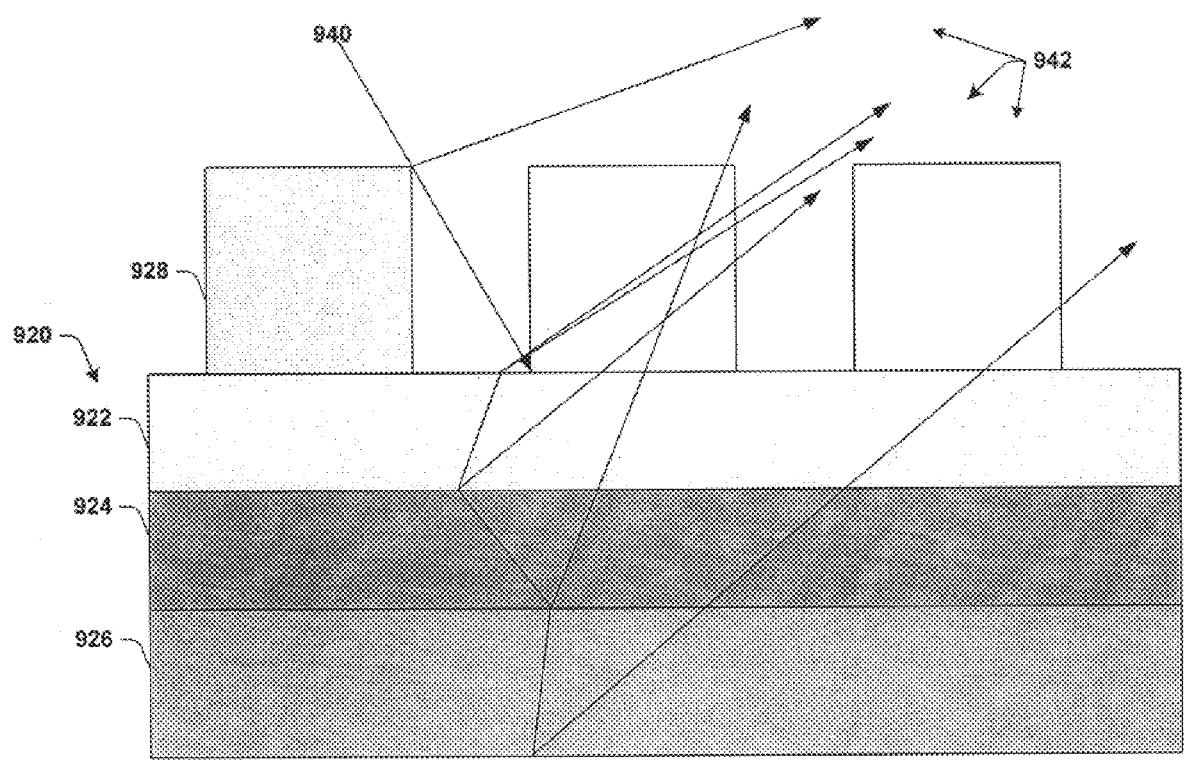
FIG. 14 illustrates a complex reflected and refracted light produced when an incident light is directed onto a surface, in accordance with an aspect of the present invention.

Turning now to FIG. 14, complex reflections and refractions of an incident light 940 are illustrated. The reflection and refraction of the incident light 940 can be affected by factors including, but not limited to, the presence of one or more features 928, and the composition of the substrate 920 upon which the features 928 reside. For example, properties of the substrate 920 including, but not limited to the thickness of a layer 922, the chemical properties of the layer 922, the opacity and/or reflectivity of the layer 922, the thickness of a layer 924, the chemical properties of the layer 924, the opacity and/or reflectivity of the layer 924, the thickness of a layer 926, the chemical properties of the layer 926, and the opacity and/or reflectivity of the layer 926 can affect the reflection and/or refraction of the incident light 940. Thus, a complex reflected and/or refracted light 942 may result from the incident light 940 interacting with the features 928, and/or the layers 922, 924 and 926. Although three layers 922, 924 and 926 are illustrated in FIG. 14, it is to be appreciated that a substrate can be formed of a greater or lesser number of such layers.

Figure 15:
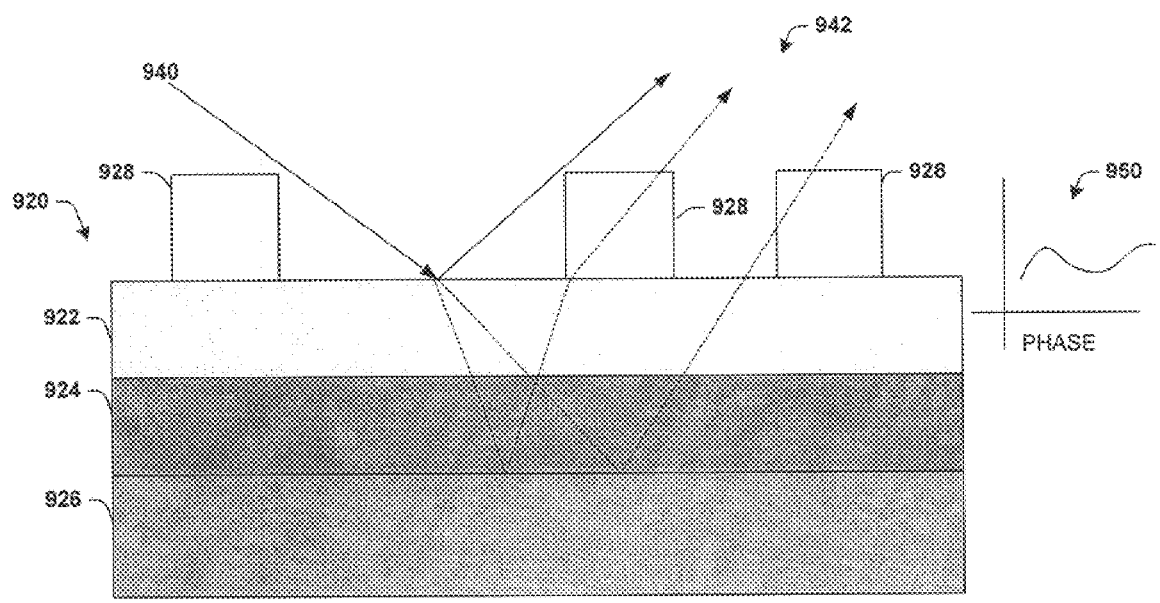
FIG. 15 illustrates a complex reflected and refracted light produced when an incident light is directed onto a surface, in accordance with an aspect of the present invention.
Figure 16:
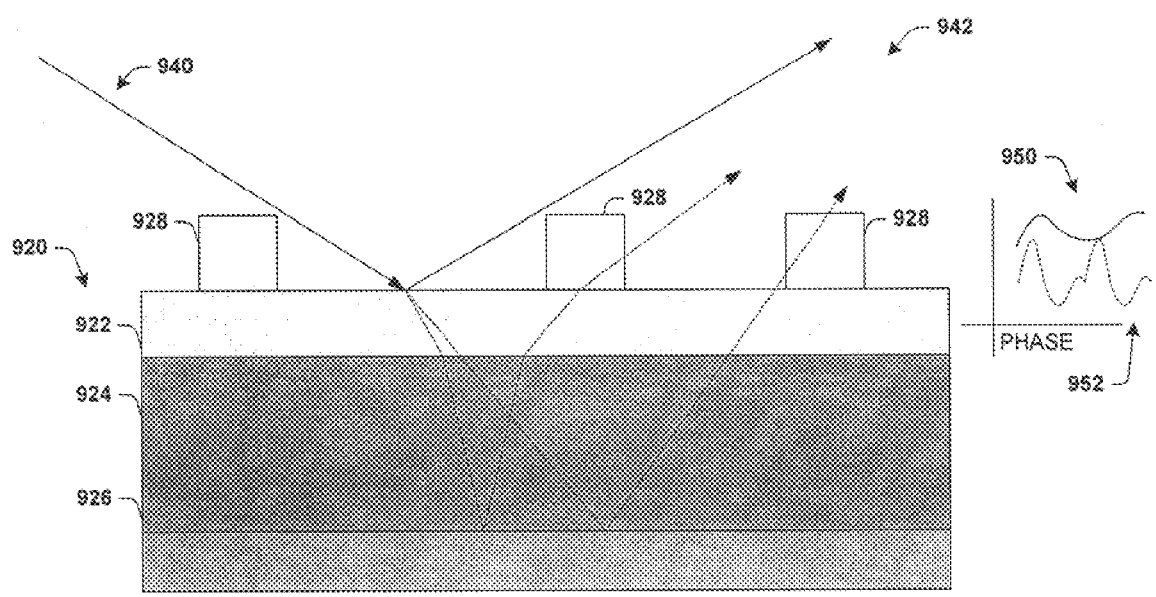
FIG. 16 illustrates a complex reflected and refracted light produced when an incident light is directed onto a surface, in accordance with an aspect of the present invention.
Figure 17:
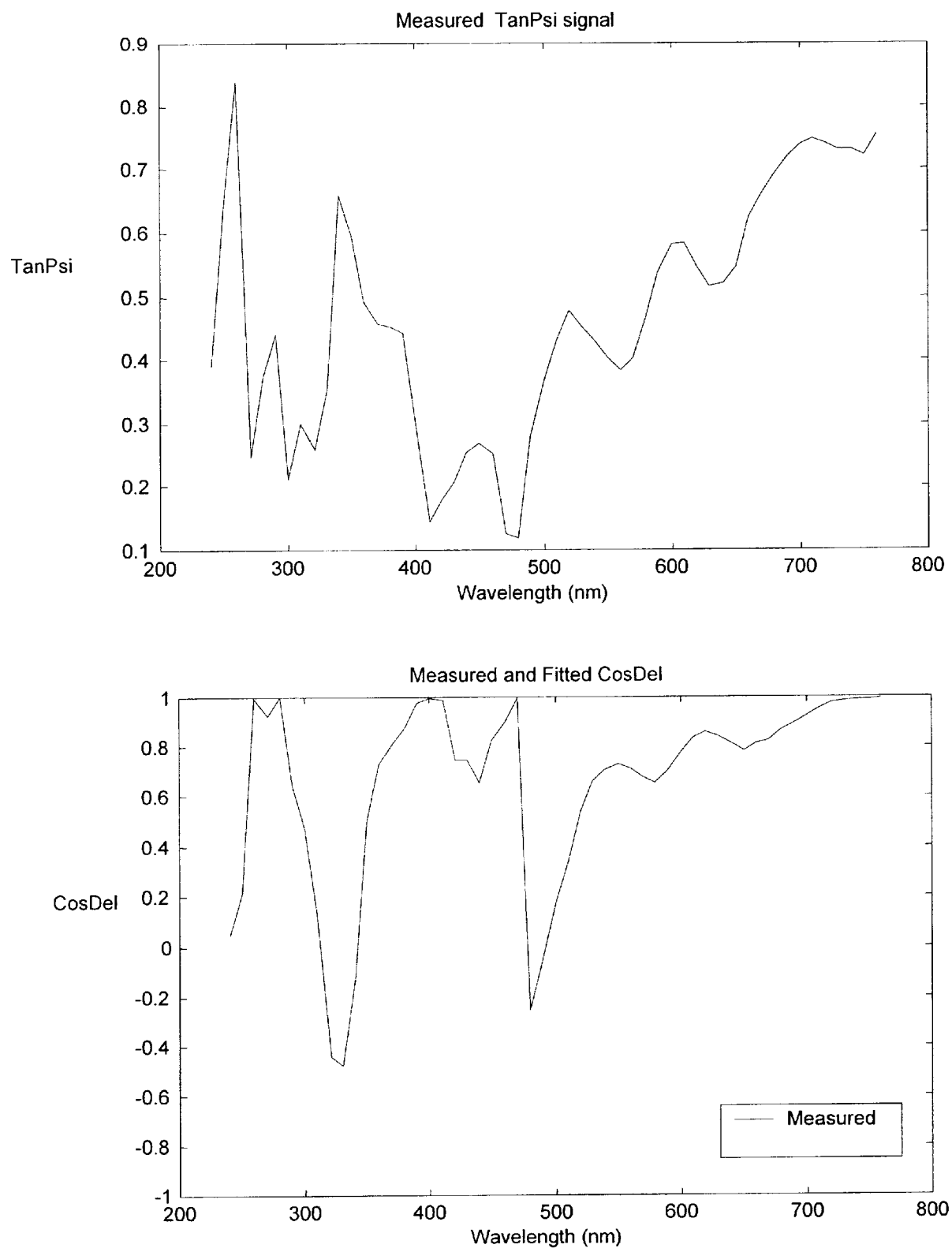
FIG. 17 illustrates phase and intensity signals recorded from a complex reflected and refracted light produced when an incident light is directed onto a surface, in accordance with an aspect of the present invention.

Turning now to FIG. 15, one of the properties from FIG. 14 is illustrated in greater detail. The substrate 920 can be formed of one or more layers 922, 924 and 926. The phase 950 of the reflected and/or refracted light 942 can depend, at least in part, on the thickness of a layer, for example, the layer 924. Thus, in FIG. 16, the phase 952 of the reflected light 942 differs from the phase 950 due, at least in part, to the different thickness of the layer 924 in FIG. 16.

Thus, scatterometry is a technique that can be employed to extract information about a surface upon which an incident light has been directed. The information can be extracted by analyzing phase and/or intensity signals of a complex reflected and/or diffracted light. The intensity and/or the phase of the reflected and/or diffracted light will change based on properties of the surface upon which the light is directed, resulting in substantially unique signatures that can be analyzed to determine one or more properties of the surface upon which the incident light was directed.

Using scatterometry in the present invention facilitates a relatively non-invasive approach to detecting gaseous phase chemical trim process progress and/or errors and to mitigating those errors in subsequent chemical trim processes.

Described above are preferred embodiments of the present invention. It is, of course, not possible to describe every conceivable combination of components or methodologies for purposes of describing the present invention, but one of ordinary skill in the art will recognize that many further combinations and permutations of the present invention are possible. Accordingly, the present invention is intended to embrace all such alterations, modifications and variations that fall within the spirit and scope of the appended claims.

What is claimed is:

1. A system for monitoring and regulating a gas based chemical trim process, comprising:
   at least one chemical trimming component operative to trim at least one portion of a wafer;
   a trim component driving system for driving the at least one chemical trimming component;
   a system for directing light toward one or more gratings located on at least one portion of the wafer;
   a trim monitoring system operable to measure one or more trim parameters from light reflected from the one or more gratings; and
   a processor operatively coupled to the trim monitoring system and the trim component driving system, wherein the processor receives a trim parameter data from the measuring system and analyzes the trim parameter data by comparing the trim parameter data to stored trim parameter data to generate a feed-forward control data operative to control the at least one chemical trimming component.

2. The system of claim 1, the trim monitoring system further including a scatterometry system for processing the light reflected from the one or more gratings.

3. The system of claim 2, the processor being operatively coupled to the scatterometry system, the processor analyzing data received from the scatterometry system and producing an analyzed data and the processor controlling, at least in part, the at least one gaseous phase chemical trimming component via the chemical trimming component driving system based, at least in part, on the analyzed data.

4. The system of claim 3, where the gas based chemical trim process is a reactive gas based chemical trim process, where a patterned photoresist is exposed to a reactive gas comprising one or more chemicals operable to trim the patterned photoresist.

5. The system of claim 4, where the reactive gas is acidic.

6. The system of claim 4, where the reactive gas is basic.

7. The system of claim 4, the processor logically mapping the wafer into one or more grid blocks and making a determination of the acceptability of trimming values in the one or more grid blocks.

8. The system of claim 7, wherein the processor determines the existence of unacceptable trimming values for at least a portion of the wafer based on comparing one or more measured trimming values to one or more stored trimming values.

9. The system of claim 8, wherein the processor employs a non-linear training system in computing feed-forward control data operable to adjust the at least one chemical trimming component.

10. A method for monitoring and regulating a gas based chemical trim process comprising:
    logically partitioning a wafer into one or more portions;
    fabricating one or more gratings on the wafer;
    exposing the wafer to a reactive gas comprising one or more chemicals, the chemicals operable to trim a patterned photoresist;
    directing an incident light onto at least one of the one or more gratings;
    collecting a reflected light reflected from the at least one grating;
    measuring the reflected light to determine one or more critical dimensions associated with the at least one grating;
    computing one or more adjustments for one or more chemical trimming components by comparing the one or more critical dimensions to scatterometry signatures associated with one or more stored critical dimensions; and
    adjusting the gaseous phase chemical trim process based, at least in part, on the one or more adjustments.

11. The method of claim 10, further comprising processing the reflected light in a scatterometry system.

12. The method of claim 11 wherein computing the one or more adjustments is based, at least in part, on data received from the scatterometry system.

13. The method of claim 12, wherein the gas based chemical trim process is regulated for portions of the wafer that have been trimmed.

14. The method of claim 12 wherein the gas based chemical trim process is regulated for portions on the wafer that have not been trimmed.

15. The method of claim 12, wherein the gas based chemical trim process is regulated for subsequent wafers.

16. The method of claim 12, where the gas based chemical trim process is a reactive gas based chemical trim process, where a patterned photoresist is exposed to a reactive gas comprising one or more chemicals operable to trim the patterned photoresist.

17. The method of claim 16, where the reactive gas is acidic.

18. The system of claim 16, where the reactive gas is basic.

19. A method for monitoring and regulating a chemical trim process comprising:
    logically partitioning a wafer into one or more grid blocks;

exposing the wafer to a gas comprising one or more trimming chemicals;

directing an incident light on at least one of the one or more grid blocks;

monitoring the chemical trim process in at least one of the one or more grid blocks by analyzing light reflected from the at least one of the one or more grid blocks; and coordinating control of at least one or more chemical trimming components based, at least in part, on the analysis of the light reflected from the at least one of the one or more grid blocks.

20. The method of claim 19, wherein the one or more grid blocks are measured at pre-determined intervals of time.

21. A system for monitoring and regulating a trim process, comprising:

means for partitioning a wafer into one or more grid blocks;

means for exposing a wafer to a gas containing one or more trimming chemical;

scatterometry means for sensing the acceptability of trimming in at least one of the one or more grid blocks;

means for controlling the trimming of a wafer portion; and means for selectivelys controlling the means for trimming.

* * * * *